(12) United States Patent
Adema et al.

(10) Patent No.: US 6,500,919 B1
(45) Date of Patent: *Dec. 31, 2002

(54) MELANOMA ASSOCIATED ANTIGENIC POLYPEPTIDE, EPITOPES THEREOF AND VACCINES AGAINST MELANOMA

(75) Inventors: Gosse Jan Adema, Nijmegen (NL); Carl Gustav Figdor, Nijmegen (NL)

(73) Assignee: IntroGene B.V., Leiden (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/388,852

(22) Filed: Feb. 15, 1995

(30) Foreign Application Priority Data

Feb. 16, 1994 (EP) .............................. 94200337
Dec. 21, 1994 (EP) .............................. 94203709

(51) Int. Cl.⁷ .............................. A61K 38/04
(52) U.S. Cl. .................. 530/328; 530/300; 530/350; 530/822; 514/2
(58) Field of Search ................... 530/822, 300, 530/328, 350; 514/2

(56) References Cited

U.S. PATENT DOCUMENTS

| | | | | |
|---|---|---|---|---|
| 4,485,086 A | * | 11/1984 | Wong | 424/1.1 |
| 5,376,531 A | * | 12/1994 | Anderson et al. | 435/7.23 |
| 5,844,075 A | * | 12/1998 | Kawakami et al. | 530/326 |

FOREIGN PATENT DOCUMENTS

EP    0174608    *   3/1986

OTHER PUBLICATIONS

MPSRCH Search Report, for Seg ID No. 21, p. 1–2, 2001.*
MPSRCH Search Report Seg ID No. 22, p. 1–3, 2001.*
Burgers et al. J. Cell Biol. 11: 2129–2138, 1990.*
Lazar et al. Mol. Cell Biol. 8: 1247–1252, 1998.*
Tao et al. J. Immunol. 143(8):2595–2601, 1989.*
Gillies et al. Human Antibod & Hybridomas: 1(1): 47–54, 1990.*
Ezzell. J. NIH Res, 7:46–49, 1995.*
Sptiler. Caucer Biotherapy 10: 1–3, 1995.*
Boon. Adv. Can Res. 58: 177–210, 1992.*
Grika, Science, 278: 1041–1042, 1997.*
Jain. Sci Am. 271: 58–65, 1994.*
Curti. Crit. Rev. Oncol/Hematol. 14 : 29–39, 1993.*
Hartwell, Science, 278: 1064–1068, 1997.*
Kawakami, PNAS 91: 6458, Jul. 1994.*
Adema, J. Biol Chem 269: 20126, Aug. 5, 1994.*
Osband, M.E. et al. 1990. Immunology Today 11(6):193–195.*
J.G. Adema et al., "Melanocyte lineage–specific antigens recognized by monoclonal antibodies NKI–beteb, HMB–50, and HMB–45, are encoded by a single cDNA," *The American Journal of Pathology*, 143:6:1579–1585 (1993).
A. Vogel, "Human 95kD melanocyte–specific secreted glycoprotein mRNA, 3' end" EMBL Database, Accession No. M32295, Nov. 26, 1990.
S.B. Kwon et al., "melanocyte–specific gene, Pmel 17, maps near the silver coat color locus on mouse chromosome 10 and is in a syntenic region on human chromosome 12," *Proceedings of the National Academy of Sciences of USA*, 88:20:9228–9232, Oct. 15, 1991, Washington D.C., USA.

* cited by examiner

Primary Examiner—Susan Ungar
Assistant Examiner—Minh-Tam Davis
(74) Attorney, Agent, or Firm—TraskBritt

(57) ABSTRACT

A melanoma associated antigen known as gp100. Furthermore, peptides derived from the antigen are described. Gp100 and its peptides can be used in vaccines for the treatment of melanoma. Another aspect of the invention is host cells capable of expressing gp100 for the gp100-derived peptides. Furthermore, tumor infiltrating lymphocytes (TIL's) specifically recognizing gp100 are described, as are vaccines with these TIL's. Also disclosed are diagnostics for the detection of melanoma and for the monitoring of vaccination.

6 Claims, 4 Drawing Sheets

FIG. 1

| Intron Size (nt) | |
|---|---|
| A | 102 |
| CATGCCTGgtaggtcc......agacacigagtgaagcagtgcctgggattcttctcacagGTCAAG | |
| A' | 81 |
| CATGCCTGgtaggtcc.........gggcagctggcaagcagcagacactgagtgaagcagTGCCTGG | |

FIG. 2

```
              #                                              #
Gp100    PLDCVLYRYGSFSVTLDIVQGIESAEILQAVPS***GEGDAFELTVSCQGGLPKEA
Pmel17   --------------------------------***---------------------
RPE1     --------------L------*S-----------S-***S----------------
MMP115   -TG--------T--TE-N-------VA-V-V--AAPE-S-NSV----T-E-S--E-V

#    #    #    #              #
Gp100    CMEISSPGCQPPAQRLCQPVLPSPACQLVLHQILKGGSGTYCLNVSLADTNSLAVV
Pmel17   --------------------------------------------------------
RPE1     --D-------L----------P-----------V---------------A----M-
MMP115   -TVVADAE-RTAQMQT-SA-A-A-G-----R-DFNQ*--L---------NG-G---A Gp100    STQLIMP*****GQEAGLGQVPLIVGILLVLMAVVLASLIYRRRLMKQDFSV
Pmel17   -------VPGILLT---------R------------------------**----
RPE1     ----V--*******------R-A--F--------T-LL-------------GSEVPL
MMP115   --HVAVGSIPSRQWHHAHRGAALGTAH-RCSGHRCLH-PPCEVQPAAAHSPHGPPA Gp100    PQLPHSSSHWLRLPRI*FCSCPIGENSPLLSGQQV
Pmel17   -----------------*-----------------
RPE1     -----GRTQ-----W*-R------SK---------
MMP115   ---AAPRCYPAFAAAPG-WGGSQWRKQ-PARANA-
```

FIG. 4
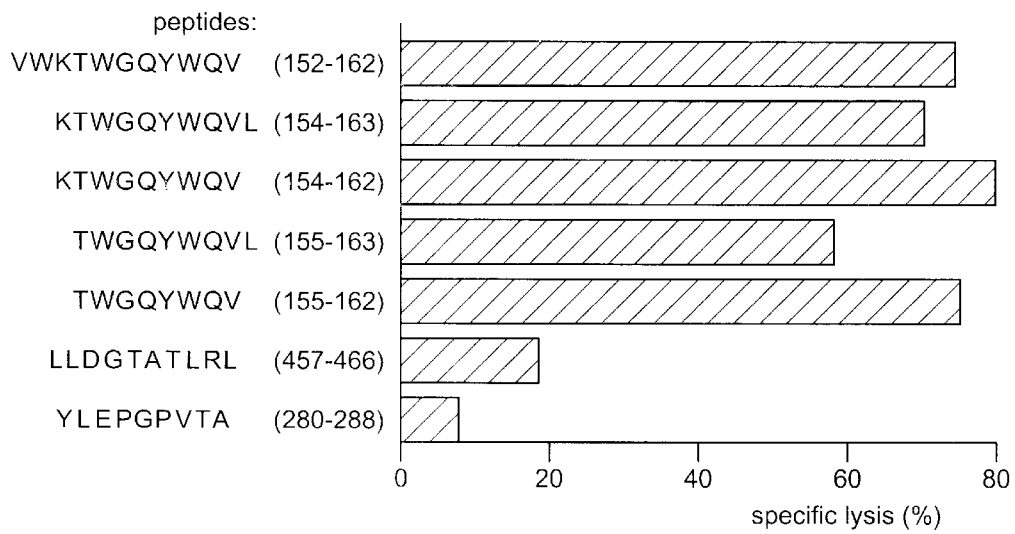
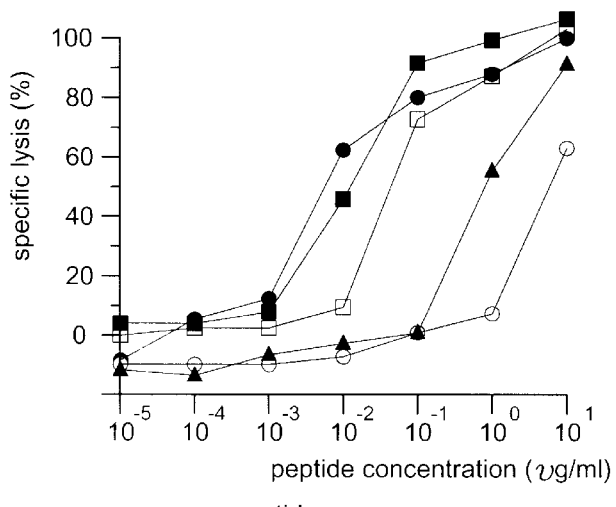

SEQUENCE LISTING (1) GENERAL INFORMATION:

(iii) NUMBER OF SEQUENCES: 38

(2) INFORMATION FOR SEQ ID NO: 1:

```
    (i) SEQUENCE CHARACTERISTICS:
        (A) LENGTH: 2115 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (F) TISSUE TYPE: Melanoma
        (G) CELL TYPE: Melanocyte (ix) FEATURE:
        (A) NAME/KEY:  CDS
        (B) LOCATION:  22...2005

(ix) FEATURE:
        (A) NAME/KEY:  misc_signal
        (B) LOCATION:  1...81

(ix) FEATURE:
        (A) NAME/KEY:  misc_feature
        (B) LOCATION:  1792...1870
        (D) OTHER INFORMATION: /function = "transmembrane region"

(ix) FEATURE:
        (A) NAME/KEY:  misc_binding
        (B) LOCATION:  262...264
        (D) OTHER INFORMATION: /bound  moiety = "carbohydrate"

(ix) FEATURE:
        (A) NAME/KEY:  misc_binding
        (B) LOCATION:  337...339
        (D) OTHER INFORMATION: /bound  moiety = "carbohydrate"

(ix) FEATURE:
        (A) NAME/KEY:  misc_binding
        (B) LOCATION:  352...354
        (D) OTHER INFORMATION: /bound  moiety = "carbohydrate"

(ix) FEATURE:
        (A) NAME/KEY:  misc_binding
        (B) LOCATION:  982...984
        (D) OTHER INFORMATION: /bound  moiety = "carbohydrate"

(ix) FEATURE:
        (A) NAME/KEY:  misc_binding
        (B) LOCATION:  1723...1725
        (D) OTHER INFORMATION: /bound  moiety = "carbohydrate"

(xi) SEQUENCE DESCRIPTION: SEQ ID NO: 1:

CGCGGAATCC GGAAGAACAC AATGGATCTG GTGCTAAAAA GATGCCTTCT TCATTTGGCT      60

GTGATAGGTG CTTTGCTGGC TGTGGGGGCT ACAAAAGTAC CCAGAAACCA GGACTGGCTT     120

GGTGTCTCAA GGCAACTCAG AACCAAAGCC TGGAACAGGC AGCTGTATCC AGAGTGGACA     180

GAAGCCCAGA GACTTGACTG CTGGAGAGGT GGTCAAGTGT CCCTCAAGGT CAGTAATGAT     240

GGGCCTACAC TGATTGGTGC AAATGCCTCC TTCTCTATTG CCTTGAACTT CCCTGGAAGC     300

CAAAAGGTAT TGCCAGATGG GCAGGTTATC TGGGTCAACA ATACCATCAT CAATGGGAGC     360

CAGGTGTGGG GAGGACAGCC AGTGTATCCC AGGAAACTG ACGATGCCTG CATCTTCCCT      420

GATGGTGGAC CTTGCCCATC TGGCTCTTGG TCTCAGAAGA GAAGCTTTGT TTATGTCTGG     480

AAGACCTGGG GCCAATACTG GCAAGTTCTA GGGGGCCCAG TGTCTGGGCT GAGCATTGGG     540

ACAGGCAGGG CAATGCTGGG CACACACACC ATGGAAGTGA CTGTCTACCA TCGCCGGGGA     600

TCCCGGAGCT ATGTGCCTCT TGCTCATTCC AGCTCAGCCT TCACCATTAC TGACCAGGTG     660

CCTTTCTCCG TGAGCGTGTC CCAGTTGCGG GCCTTGGATG GAGGGAACAA GCACTTCCTG     720
```

-continued

```
AGAAATCAGC CTCTGACCTT TGCCCTCCAG CTCCATGACC CCAGTGGCTA TCTGGCTGAA      780

GCTGACCTCT CCTACACCTG GGACTTTGGA GACAGTAGTG GAACCCTGAT CTCTCGGGCA      840

CTTGTGGTCA CTCATACTTA CCTGGAGCCT GGCCCAGTCA CTGCCCAGGT GGTCCTGCAG      900

GCTGCCATTC CTCTCACCTC CTGTGGCTCC TCCCCAGTTC CAGGCACCAC AGATGGGCAC      960

AGGCCAACTG CAGAGGCCCC TAACACCACA GCTGGCCAAG TGCCTACTAC AGAAGTTGTG     1020

GGTACTACAC CTGGTCAGGC GCCAACTGCA GAGCCCTCTG AACCACATC  TGTGCAGGTG     1080

CCAACCACTG AAGTCATAAG CACTGCACCT GTGCAGATGC CAACTGCAGA GAGCACAGGT     1140

ATGACACCTG AGAAGGTGCC AGTTTCAGAG GTCATGGGTA CCACACTGGC AGAGATGTCA     1200

ACTCCAGAGG CTACAGGTAT GACACCTGCA GAGGTATCAA TTGTGGTGCT TTCTGGAACC     1260

ACAGCTGCAC AGGTAACAAC TACAGAGTGG GTGGAGACCA CAGCTAGAGA GCTACCTATC     1320

CCTGAGCCTG AAGGTCCAGA TGCCAGCTCA ATCATGTCTA CGGAAAGTAT TACAGGTTCC     1380

CTGGGCCCCC TGCTGGATGG TACAGCCACC TTAAGGCTGG TGAAGAGACA AGTCCCCCTG     1440

GATTGTGTTC TGTATCGATA TGGTTCCTTT TCCGTCACCC TGGACATTGT CCAGGGTATT     1500

GAAAGTGCCG AGATCCTGCA GGCTGTGCCG TCCGGTGAGG GGGATGCATT TGAGCTGACT     1560

GTGTCCTGCC AAGGCGGGCT GCCCAAGGAA GCCTGCATGG AGATCTCATC GCCAGGGTGC     1620

CAGCCCCCTG CCCAGCGGCT GTGCCAGCCT GTGCTACCCA GCCCAGCCTG CCAGCTGGTT     1680

CTGCACCAGA TACTGAAGGG TGGCTCGGGG ACATACTGCC TCAATGTGTC TCTGGCTGAT     1740

ACCAACAGCC TGGCAGTGGT CAGCACCCAG CTTATCATGC CTGGTCAAGA AGCAGGCCTT     1800

GGGCAGGTTC CGCTGATCGT GGGCATCTTG CTGGTGTTGA TGGCTGTGGT CCTTGCATCT     1860

CTGATATATA GGCGCAGACT TATGAAGCAA GACTTCTCCG TACCCCAGTT GCCACATAGC     1920

AGCAGTCACT GGCTGCGTCT ACCCCGCATC TTCTGCTCTT GTCCCATTGG TGAGAATAGC     1980

CCCCTCCTCA GTGGGCAGCA GGTCTGAGTA CTCTCATATG ATGCTGTGAT TTTCCTGGAG     2040

TTGACAGAAA CACCTATATT TCCCCCAGTC TTCCCTGGGA GACTACTATT AACTGAAATA     2100

AATACTCAGA GCCTG                                                     2115
```

(2) INFORMATION FOR SEQ ID NO: 2:

(i) SEQUENCE CHARACTERISTICS:
        (A) LENGTH: 661 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 2:

```
Met Asp Leu Val Leu Lys Arg Cys Leu Leu His Leu Ala Val Ile Gly
 1               5                  10                  15

Ala Leu Leu Ala Val Gly Ala Thr Lys Val Pro Arg Asn Gln Asp Trp
             20                  25                  30

Leu Gly Val Ser Arg Gln Leu Arg Thr Lys Ala Trp Asn Arg Gln Leu
         35                  40                  45

Tyr Pro Glu Trp Thr Glu Ala Gln Arg Leu Asp Cys Trp Arg Gly Gly
     50                  55                  60

Gln Val Ser Leu Lys Val Ser Asn Asp Gly Pro Thr Leu Ile Gly Ala
```

-continued

```
              65                  70                  75                  80
Asn Ala Ser Phe Ser Ile Ala Leu Asn Phe Pro Gly Ser Gln Lys Val
                85                  90                  95
Leu Pro Asp Gly Gln Val Ile Trp Val Asn Asn Thr Ile Ile Asn Gly
               100                 105                 110
Ser Gln Val Trp Gly Gly Gln Pro Val Tyr Pro Gln Glu Thr Asp Asp
               115                 120                 125
Ala Cys Ile Phe Pro Asp Gly Pro Cys Pro Ser Gly Ser Trp Ser
               130                 135                 140
Gln Lys Arg Ser Phe Val Tyr Val Trp Lys Thr Trp Gly Gln Tyr Trp
145                 150                 155                 160
Gln Val Leu Gly Gly Pro Val Ser Gly Leu Ser Ile Gly Thr Gly Arg
               165                 170                 175
Ala Met Leu Gly Thr His Thr Met Glu Val Thr Val Tyr His Arg Arg
               180                 185                 190
Gly Ser Arg Ser Tyr Val Pro Leu Ala His Ser Ser Ala Phe Thr
               195                 200                 205
Ile Thr Asp Gln Val Pro Phe Ser Val Ser Val Ser Gln Leu Arg Ala
               210                 215                 220
Leu Asp Gly Gly Asn Lys His Phe Leu Arg Asn Gln Pro Leu Thr Phe
225                 230                 235                 240
Ala Leu Gln Leu His Asp Pro Ser Gly Tyr Leu Ala Glu Ala Asp Leu
               245                 250                 255
Ser Tyr Thr Trp Asp Phe Gly Asp Ser Ser Gly Thr Leu Ile Ser Arg
               260                 265                 270
Ala Leu Val Val Thr His Thr Tyr Leu Glu Pro Gly Pro Val Thr Ala
               275                 280                 285
Gln Val Val Leu Gln Ala Ala Ile Pro Leu Thr Ser Cys Gly Ser Ser
               290                 295                 300
Pro Val Pro Gly Thr Thr Asp Gly His Arg Pro Thr Ala Glu Ala Pro
305                 310                 315                 320
Asn Thr Thr Ala Gly Gln Val Pro Thr Thr Glu Val Val Gly Thr Thr
               325                 330                 335
Pro Gly Gln Ala Pro Thr Ala Glu Pro Ser Gly Thr Thr Ser Val Gln
               340                 345                 350
Val Pro Thr Thr Glu Val Ile Ser Thr Ala Pro Val Gln Met Pro Thr
               355                 360                 365
Ala Glu Ser Thr Gly Met Thr Pro Glu Lys Val Pro Val Ser Glu Val
               370                 375                 380
Met Gly Thr Thr Leu Ala Glu Met Ser Thr Pro Glu Ala Thr Gly Met
385                 390                 395                 400
Thr Pro Ala Glu Val Ser Ile Val Val Leu Ser Gly Thr Thr Ala Ala
               405                 410                 415
Gln Val Thr Thr Thr Glu Trp Val Glu Thr Thr Ala Arg Glu Leu Pro
               420                 425                 430
Ile Pro Glu Pro Glu Gly Pro Asp Ala Ser Ser Ile Met Ser Thr Glu
               435                 440                 445
Ser Ile Thr Gly Ser Leu Gly Pro Leu Leu Asp Gly Thr Ala Thr Leu
               450                 455                 460
Arg Leu Val Lys Arg Gln Val Pro Leu Asp Cys Val Leu Tyr Arg Tyr
465                 470                 475                 480
Gly Ser Phe Ser Val Thr Leu Asp Ile Val Gln Gly Ile Glu Ser Ala
               485                 490                 495
```

```
Glu Ile Leu Gln Ala Val Pro Ser Gly Glu Gly Asp Ala Phe Glu Leu
            500                 505                 510

Thr Val Ser Cys Gln Gly Gly Leu Pro Lys Glu Ala Cys Met Glu Ile
            515                 520                 525

Ser Ser Pro Gly Cys Gln Pro Ala Gln Arg Leu Cys Gln Pro Val
            530                 535                 540

Leu Pro Ser Pro Ala Cys Gln Leu Val Leu His Gln Ile Leu Lys Gly
545                 550                 555                 560

Gly Ser Gly Thr Tyr Cys Leu Asn Val Ser Leu Ala Asp Thr Asn Ser
                565                 570                 575

Leu Ala Val Val Ser Thr Gln Leu Ile Met Pro Gly Gln Glu Ala Gly
            580                 585                 590

Leu Gly Gln Val Pro Leu Ile Val Gly Ile Leu Leu Val Leu Met Ala
            595                 600                 605

Val Val Leu Ala Ser Leu Ile Tyr Arg Arg Arg Leu Met Lys Gln Asp
            610                 615                 620

Phe Ser Val Pro Gln Leu Pro His Ser Ser Ser His Trp Leu Arg Leu
625                 630                 635                 640

Pro Arg Ile Phe Cys Ser Cys Pro Ile Gly Glu Asn Ser Pro Leu Leu
                645                 650                 655

Ser Gly Gln Gln Val
            660

(2) INFORMATION FOR SEQ ID NO: 3:

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (ix) FEATURE:
        (A) NAME/KEY:  CDS
        (B) LOCATION:  1...30

(xi) SEQUENCE DESCRIPTION: SEQ ID NO: 3:

CTGCTGGATG GTACAGCCAC CTTAAGGCTG                                    30

(2) INFORMATION FOR SEQ ID NO: 4:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 4:

Leu Leu Asp Gly Thr Ala Thr Leu Arg Leu
1               5                   10

(2) INFORMATION FOR SEQ ID NO: 5:
```

(i) SEQUENCE CHARACTERISTICS:
        (A) LENGTH: 30 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1...30

(xi) SEQUENCE DESCRIPTION: SEQ ID NO: 5:

GTATTGCCAG ATGGGCAGGT TATCTGGGTC                                               30

(2) INFORMATION FOR SEQ ID NO: 6:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 6:

Val Leu Pro Asp Gly Gln Val Ile Trp Val
1               5                   10

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (F) TISSUE TYPE: Melanoma
        (G) CELL TYPE: Melanocyte (ix) FEATURE:
        (A) NAME/KEY: CDS
        (B) LOCATION: 1...24

(xi) SEQUENCE DESCRIPTION: SEQ ID NO: 7:

ACCTGGGGCC AATACTGGCA AGTT                                                     24

(2) INFORMATION FOR SEQ ID NO: 8:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 8:

Thr Trp Gly Gln Tyr Trp Gln Val
1               5

(2) INFORMATION FOR SEQ ID NO: 9:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (F) TISSUE TYPE: Melanoma
        (G) CELL TYPE: Melanocyte (ix) FEATURE:
        (A) NAME/KEY:  CDS
        (B) LOCATION:   1...36

(ix) FEATURE:
        (A) NAME/KEY:  protein bind
        (B) LOCATION:   1...33

(ix) FEATURE:
        (A) NAME/KEY:  protein bind
        (B) LOCATION:   1...36

(ix) FEATURE:
        (A) NAME/KEY:  protein bind
        (B) LOCATION:   7...33

(ix) FEATURE:
        (A) NAME/KEY:  protein bind
        (B) LOCATION:   10...36

(xi) SEQUENCE DESCRIPTION: SEQ ID NO: 9:

GTCTGGAAGA CCTGGGGCCA ATACTGGCAA GTTCTA                                36

(2) INFORMATION FOR SEQ ID NO: 10:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 10:

Val Trp Lys Thr Trp Gly Gln Tyr Trp Gln Val Leu
1               5                   10

(2) INFORMATION FOR SEQ ID NO: 11:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (ix) FEATURE:
              (A) NAME/KEY: misc feature
              (B) LOCATION:    7...12
              (D) OTHER INFORMATION: /label = EcoRI-site (xi) SEQUENCE DESCRIPTION: SEQ ID NO: 11:

TATCTAGAAT TCTGCACCAG ATACTGAAG                                                29

(2) INFORMATION FOR SEQ ID NO: 12:

(i) SEQUENCE CHARACTERISTICS:
              (A) LENGTH: 32 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (ix) FEATURE:
              (A) NAME/KEY: misc feature
              (B) LOCATION:    7...12
              (D) OTHER INFORMATION: /label = EcoRI-site (xi) SEQUENCE DESCRIPTION: SEQ ID NO: 12:

TATCTAGAAT TCTGCAAGAT GCCCACGATC AG                                            32

(2) INFORMATION FOR SEQ ID NO: 13:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 13:

CTTCTTGACC AGGCATGATA                                                          20

(2) INFORMATION FOR SEQ ID NO: 14:

(i) SEQUENCE CHARACTERISTICS:
              (A) LENGTH: 20 base pairs
              (B) TYPE: nucleic acid
              (C) STRANDEDNESS: single
              (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 14:

TGTGAGAAGA ATCCCAGGCA                                                          20

(2) INFORMATION FOR SEQ ID NO: 15:

(i) SEQUENCE CHARACTERISTICS:

(A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 15:

GCTTATCATG CCTGTGCCTG GATTCTTCTC ACAGGT                                  36

(2) INFORMATION FOR SEQ ID NO: 16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 16:

CATGGAAGTG ACTGTCTACC                                                    20

(2) INFORMATION FOR SEQ ID NO: 17:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 17:

CTGAGCGAAT TCGGAACCTG TAATACTTTC CG                                      32

(2) INFORMATION FOR SEQ ID NO: 18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 18:

CTGAGCGAAT TCGTGAAGAG ACAAGTCCCC C                                       31

(2) INFORMATION FOR SEQ ID NO: 19:

(i) SEQUENCE CHARACTERISTICS:
        (A) LENGTH: 22 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 19:

TCACAGCATC ATATGAGAGT AC                                              22

(2) INFORMATION FOR SEQ ID NO: 20:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 20:

Val Trp Lys Thr Trp Gly Gln Tyr Trp Gln Val
1               5                   10

(2) INFORMATION FOR SEQ ID NO: 21:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 21:

Lys Thr Trp Gly Gln Tyr Trp Gln Val Leu
1               5                   10

(2) INFORMATION FOR SEQ ID NO: 22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 22:

Lys Thr Trp Gly Gln Tyr Trp Gln Val
1               5

(2) INFORMATION FOR SEQ ID NO: 23:

(i) SEQUENCE CHARACTERISTICS:
        (A) LENGTH: 9 amino acids
        (B) TYPE: amino acid
        (C) STRANDEDNESS: single (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 23:

Thr Trp Gly Gln Tyr Trp Gln Val Leu
1               5

(2) INFORMATION FOR SEQ ID NO: 24:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 24:

Met Leu Gly Thr His Thr Met Glu Val
1               5

(2) INFORMATION FOR SEQ ID NO: 25:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 25:

Arg Leu Met Lys Gln Asp Phe Ser Val
1               5

(2) INFORMATION FOR SEQ ID NO: 26:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 26:

TATTGAAAGT GCCGAGATCC                                         20

(2) INFORMATION FOR SEQ ID NO: 27:

(i) SEQUENCE CHARACTERISTICS:
          (A) LENGTH: 19 base pairs
          (B) TYPE: nucleic acid
          (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 27:

TGCAAGGACC ACAGCCATC                                            19

(2) INFORMATION FOR SEQ ID NO: 28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 28:

GCACAGGCCA ACTGCAGA                                             18

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 29:

TTCAGTATCT GGTGCAGAAC                                           20

(2) INFORMATION FOR SEQ ID NO: 30:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO: 30:

Tyr Leu Glu Pro Gly Pro Val Thr Ala
1               5

(2) INFORMATION FOR SEQ ID NO: 31:

(i) SEQUENCE CHARACTERISTICS:
        (A) LENGTH: 6 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO: 31:

AATAAA                                                                                  6

(2) INFORMATION FOR SEQ ID NO: 32:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 32:

Arg Ile Gln Thr
1

(2) INFORMATION FOR SEQ ID NO: 33:

(i) SEQUENCE CHARACTERISTICS:
            (A) LENGTH: 61 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:
            (A) NAME/KEY: exon
            (B) LOCATION:   1...8

(ix) FEATURE:
            (A) NAME/KEY: intron
            (B) LOCATION:   9...55

(ix) FEATURE:
            (A) NAME/KEY: exon
            (B) LOCATION:   56...61

(xi) SEQUENCE DESCRIPTION: SEQ ID NO: 33:

CATGCCTGGT AGGTCCAGAC ACTGAGTGAA GCAGTGCCTG GGATTCTTCT CACAGGTCAA       60
G                                                                      61

(2) INFORMATION FOR SEQ ID NO: 34:

(i) SEQUENCE CHARACTERISTICS:
            (A) LENGTH: 59 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (ix) FEATURE:

(A) NAME/KEY: exon
        (B) LOCATION: 1...8

(ix) FEATURE:
        (A) NAME/KEY: intron
        (B) LOCATION: 9...52

(ix) FEATURE:
        (A) NAME/KEY: exon
        (B) LOCATION: 53...59

(xi) SEQUENCE DESCRIPTION: SEQ ID NO: 34:

CATGCCTGGT AGGTCCGGGC AGCTGGCAAG CAGCAGACAC TGAGTGAAGC AGTGCCTGG    59

(2) INFORMATION FOR SEQ ID NO: 35:

(i) SEQUENCE CHARACTERISTICS:
        (A) LENGTH: 190 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 35:

Pro Leu Asp Cys Val Leu Tyr Arg Tyr Gly Ser Phe Ser Val Thr Leu
1               5                   10                  15

Asp Ile Val Gln Gly Ile Glu Ser Ala Glu Ile Leu Gln Ala Val Pro
            20                  25                  30

Ser Gly Glu Gly Asp Ala Phe Glu Leu Thr Val Ser Cys Gln Gly Gly
        35                  40                  45

Leu Pro Lys Glu Ala Cys Met Glu Ile Ser Ser Pro Gly Cys Gln Pro
    50                  55                  60

Pro Ala Gln Arg Leu Cys Gln Pro Val Leu Pro Ser Pro Ala Cys Gln
65                  70                  75                  80

Leu Val Leu His Gln Ile Leu Lys Gly Gly Ser Gly Thr Tyr Cys Leu
                85                  90                  95

Asn Val Ser Leu Ala Asp Thr Asn Ser Leu Ala Val Val Ser Thr Gln
            100                 105                 110

Leu Ile Met Pro Gly Gln Glu Ala Gly Leu Gly Gln Val Pro Leu Ile
        115                 120                 125

Val Gly Ile Leu Leu Val Leu Met Ala Val Val Leu Ala Ser Leu Ile
    130                 135                 140

Tyr Arg Arg Arg Leu Met Lys Gln Asp Phe Ser Val Pro Gln Leu Pro
145                 150                 155                 160

His Ser Ser Ser His Trp Leu Arg Leu Pro Arg Ile Phe Cys Ser Cys
                165                 170                 175

Pro Ile Gly Glu Asn Ser Pro Leu Leu Ser Gly Gln Gln Val
            180                 185                 190

(2) INFORMATION FOR SEQ ID NO: 36:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 36:

```
Pro Leu Asp Cys Val Leu Tyr Arg Tyr Gly Ser Phe Ser Val Thr Leu
1               5                   10                  15

Asp Ile Val Gln Gly Ile Glu Ser Ala Glu Ile Leu Gln Ala Val Pro
            20                  25                  30

Ser Gly Glu Gly Asp Ala Phe Glu Leu Thr Val Ser Cys Gln Gly Gly
        35                  40                  45

Leu Pro Lys Glu Ala Cys Met Glu Ile Ser Ser Pro Gly Cys Gln Pro
    50                  55                  60

Pro Ala Gln Arg Leu Cys Gln Pro Val Leu Pro Ser Pro Ala Cys Gln
65                  70                  75                  80

Leu Val Leu His Gln Ile Leu Lys Gly Gly Ser Gly Thr Tyr Cys Leu
                85                  90                  95

Asn Val Ser Leu Ala Asp Thr Asn Ser Leu Ala Val Val Ser Thr Gln
            100                 105                 110

Leu Ile Met Pro Val Pro Gly Ile Leu Leu Thr Gly Gln Glu Ala Gly
        115                 120                 125

Leu Gly Gln Val Arg Leu Ile Val Gly Ile Leu Leu Val Leu Met Ala
    130                 135                 140

Val Val Leu Ala Ser Leu Ile Tyr Arg Arg Arg Leu Met Lys Gln Asp
145                 150                 155                 160

Phe Ser Val Pro Gln Leu Pro His Ser Ser Ser His Trp Leu Arg Leu
                165                 170                 175

Pro Arg Ile Phe Cys Ser Cys Pro Ile Gly Glu Asn Ser Pro Leu Leu
            180                 185                 190

Ser Gly Gln Gln Val
        195
```

(2) INFORMATION FOR SEQ ID NO: 37:

(i) SEQUENCE CHARACTERISTICS:
        (A) LENGTH: 192 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 37:

```
Pro Leu Asp Cys Val Leu Tyr Arg Tyr Gly Ser Phe Ser Leu Thr Leu
1               5                   10                  15

Asp Ile Val Gln Ser Ile Glu Ser Ala Glu Ile Leu Gln Ala Val Ser
            20                  25                  30

Ser Ser Glu Gly Asp Ala Phe Glu Leu Thr Val Ser Cys Gln Gly Gly
        35                  40                  45

Leu Pro Lys Glu Ala Cys Met Asp Ile Ser Ser Pro Gly Cys Gln Leu
    50                  55                  60

Pro Ala Gln Arg Leu Cys Gln Pro Val Pro Ser Pro Ala Cys Gln
65                  70                  75                  80

Leu Val Leu His Gln Val Leu Lys Gly Gly Ser Gly Thr Tyr Cys Leu
                85                  90                  95
```

```
Asn Val Ser Leu Ala Asp Ala Asn Ser Leu Ala Met Val Ser Thr Gln
                100                 105                 110
Leu Val Met Pro Gly Gln Glu Ala Gly Leu Arg Gln Ala Pro Leu Phe
            115                 120                 125
Val Gly Ile Leu Leu Val Leu Thr Ala Leu Leu Leu Ala Ser Leu Ile
        130                 135                 140
Tyr Arg Arg Arg Leu Met Lys Gln Gly Ser Glu Val Pro Leu Pro Gln
145                 150                 155                 160
Leu Pro His Gly Arg Thr Gln Trp Leu Arg Leu Trp Val Ile Phe Arg
                165                 170                 175
Ser Cys Pro Ile Gly Glu Ser Lys Pro Leu Leu Ser Gly Gln Gln Val
                180                 185                 190
```

(2) INFORMATION FOR SEQ ID NO: 38:

(i) SEQUENCE CHARACTERISTICS:
        (A) LENGTH: 202 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 38:

```
Pro Thr Gly Cys Val Leu Tyr Arg Tyr Gly Thr Phe Ser Thr Glu Leu
1               5                   10                  15
Asn Ile Val Gln Gly Ile Glu Ser Val Ala Ile Val Gln Val Val Pro
            20                  25                  30
Ala Ala Pro Glu Gly Ser Gly Asn Ser Val Glu Leu Thr Val Thr Cys
        35                  40                  45
Glu Gly Ser Leu Pro Glu Glu Val Cys Thr Val Ala Asp Ala Glu
    50                  55                  60
Cys Arg Thr Ala Gln Met Gln Thr Cys Ser Ala Val Ala Pro Ala Pro
65                  70                  75                  80
Gly Cys Gln Leu Val Leu Arg Gln Asp Phe Asn Gln Ser Gly Leu Tyr
                85                  90                  95
Cys Leu Asn Val Ser Leu Ala Asn Gly Asn Gly Leu Ala Val Ala Ser
                100                 105                 110
Thr His Val Ala Val Gly Ser Ile Pro Ser Arg Gln Trp His His Ala
            115                 120                 125
His Arg Gly Ala Ala Leu Gly Thr Ala His Gly Arg Cys Ser Gly His
        130                 135                 140
Arg Cys Leu His Leu Pro Pro Cys Glu Val Gln Pro Ala Ala His
145                 150                 155                 160
Ser Pro His Gly Pro Pro Ala Pro Gln Leu Ala Ala Pro Arg Cys Tyr
                165                 170                 175
Pro Ala Phe Ala Ala Ala Pro Gly Phe Trp Gly Gly Ser Gln Trp Arg
            180                 185                 190
Lys Gln Pro Pro Ala Arg Ala Asn Ala Val
            195                 200
```

MELANOMA ASSOCIATED ANTIGENIC POLYPEPTIDE, EPITOPES THEREOF AND VACCINES AGAINST MELANOMA

The present invention is concerned with cancer treatment and diagnosis, especially with a melanoma associated antigen, epitopes thereof, vaccines against melanoma, tumor infiltrating T lymphocytes recognizing the antigen and diagnostics for the detection of melanoma and for the monitoring of vaccination.

Tumor cells may emancipate themselves from restrictive growth control by oncogene activation, and/or by the inactivation of tumor suppression genes. The course of tumor progression proceeds by a series of gradual, stepwise changes in different 'unit characteristics', i.e. phenotypic traits, many of which are known to be determined or at least influenced by the altered expression of defined oncogenes and/or tumor suppressive genes. Emancipation of the cell from immunological host restriction may follow multistep pathways similar to the emancipation from growth control.

A problem often encountered in cancer immunotherapy is the lack of immunogenicity of the tumor. This escape of the immune control system can be understood on basis of phenotype differences encountered in neoplastic cells (differences found in Burkitt's lymphoma cells according to Klein, G. and Boon, T., Curr. Opinion in Immunol. 5, 687–692, 1993):
decreased ability to process and present antigens;
decreased ability to stimulate autologous T cells;
complete downregulation of immunogenic proteins associated with transformed cells;
no or low expression of leukocyte adhesion molecules or other accessory molecules; and
selective downregulation of certain MHC class I and class II alleles.

MHC Class I/II antigens are often downregulated in solid tumors. This may affect all class I/II antigens, or only part of them. Viral and cellular peptides that can sensitize appropriate target cells for cytotoxic T lymphocyte mediated lysis may fail to do so when produced in cells with a low level of expression of MHC class I antigen. Cytotoxic sensitivity may be induced, at least in some cases by raising the level of MHC class I/II antigen expression by interferon γ and tumor necrosis factor α.

However, during the stepwise changes from normal to tumor tissue tumor-associated antigens appear. These antigens can be exposed through various mechanisms:
they can be molecules that are masked in some way during normal cell development, but where the neoplastic change induces removal of the masking protection for the immunosystem;
deletion of some molecules from the plasma membrane may alter the profile of adjacent molecules in a given membrane patch, and thus, in effect generate a new profile that might become immunogenic to the host;
a membrane alteration accompanying neoplastic transformation may expose new, previously hidden regions of a molecule, or may result in addition of new structural features to an existing molecule.
shedding and disintegration of tumor cells may expose the immune system to nuclear, nucleolar, or cytoplasmic components that are normally hidden in the cell.

The characteristics of tumor-associated antigens are very much dependent on the origin of the tumor carrying them. The existence of antigens associated with animal tumors was documented in the last century, and the antigenic character of human cancers has been well established, primarily through recent studies with monoclonal antibodies.

Attempts to isolate and chemically characterize these antigens have encountered serious difficulties, many having to do with a lack of reagents suitable for precipitation of the antigen-bearing molecules from a solution.

Like many other stimuli, the tumor-associated antigens activate not one but a whole set of defense mechanisms—both specific and unspecific, humoral and cellular. The dominant role in in vivo resistance to tumor growth is played by T lymphocytes. These cells recognize tumor-associated antigens presented to them by antigen presenting cells (APC's), and will be activated by this recognition, and upon activation and differentiation, attack and kill the tumor cells. A special class of these sort of lymphocytes is formed by the tumor infiltrating lymphocytes (TIL's) which can be found in solid tumors.

It has already been suggested (EP 147,689) to activate T lymphocytes with an antigenic substance linked to an insoluble carrier in vitro and then to administer these activated lymphocytes to a tumor patient.

Conventional chemotherapy is relatively ineffective in the treatment of patients with metastasic melanoma, and approximately 6000 patients die of this disease in the United States each year.

Rosenberg et al. (New Eng. J. Med. 319(25), 1676–1681, 1988) have shown the beneficial effect of immunotherapy with autologous TIL's and interleukin-2 (IL-2) in melanoma patients.

This therapy constitutes of resection of the tumor deposit, isolation of the TIL's, in vitro expansion of the TIL's and infusion into the patient under concurrent treatment of high and toxicity inducing doses of IL-2.

The TIL's used by Rosenberg are directed to and able to recognize melanoma-associated antigens.

It has been our goal to isolate such a melanoma-associated antigen in order to be able to use the antigen and/or its epitopes for the development of an immunotherapy for melanoma patients.

Melanoma antigens have already been described by Old, L. (1981) who identified 6 antigenic glycoproteins and 3 glycolipids occurring in 120 melanoma cell lines.

Also vaccines with melanoma antigens have been described: in U.S. Pat. Nos. 5,030,621 and 5,194,384 a polyvalent vaccine has been made by culturing melanoma cells and subsequent isolation of excreted melanoma-specific antigens from the culture medium.

Some specific antigens have already been proposed for therapy and diagnosis of melanoma type of cancer: the peptide p97 has been disclosed in U.S. Pat. Nos. 5,262,177 and 5,141,742, while a 35 kD protein has been mentioned in EP 529,007.

SUMMARY OF THE INVENTION

We now have found a melanoma-associated polypeptide, characterized in that it comprises the aminoacid sequence of SEQ ID NO: 2.

This melanocyte lineage-specific antigenic polypeptide (also mentioned gp100) is recognized by the monoclonal antibody NKI-beteb, which antibody has proven suitable for diagnostic purposes. The antigens recognized by this antibody are intracellular proteins of approximately 10 kd (gp 10) and 100 kd (gp100). The latter is also detectable in a culture medium of melanoma cells (Vennegoor, C. et al, Am. J. Pathol. 130, 179–192, 1988). It has also been found that the gp100 antigen reacts with other melanoma-specific antibodies such as HMB-50 (described by Vogel, A. M. and Esclamado, R. M., Cancer Res. 48, 1286–1294, 1988) or HMB-45 (described by Gown, A. M. et al., Am. J. Pathol.

123, 195–203, 1986). Since the proteins reacting with these monoclonal antibodies have been shown te be glycosylated in melanoma cells, differences have been found in mobility when analyzed by SDS-PAGE.

Although this gp100 antigen is predominantly expressed intracellularly, it has now been established that it is a suitable immunogenic antigen, because it has been demonstrated that these intracellular proteins can be processed and presented as peptides in the context of MHC molecules to cells of the immune system. In fact, tumor infiltrating lymphocytes derived from tumors of melanoma patients have been found which react with the antigen.

Therefore, the gp100 polypeptide is a potential target for cellular responses against carcinoma and thus a suitable subject for therapy and diagnosis in melanoma patients.

Gp100 is a type I transmembrane protein, which has a threonine-rich domain containing repetitive amino acid sequences present in the middle of the protein (amino acids 309–427). This threonine-rich domain, which may be subjected to extensive O-linked glycosylation, is preceded by a histidine-rich region (amino acids 182–313) and followed by a cysteine-rich domain (amino acids 475–566). Based on hydrophobicity plot analysis (Kyte, J. and Doolittle, R. F., 1982), a single transmembrane domain bordered by charged residues is present in the carboxy-terminal part (amino acids 591–611) of gp100. The predicted cytoplasmic domain is 45 amino acids long. Five putative N-linked glycosylation sites are present, consistent with gp100 being a glycoprotein.

The term "polypeptide" refers to a molecular chain of amino acids, does not refer to a specific length of the product and if required can be modified in vivo or in vitro, for example by glycosylation, amidation, carboxylation or phosphorylation; thus inter alia peptides, oligopeptides and proteins are included within the definition of polypeptide.

Of course, functional derivatives as well as fragments of the polypeptide according to the invention are also included in the present invention. Functional derivatives are meant to include polypeptides which differ in one or more amino acids in the overall sequence, which have deletions, substitutions, inversions or additions. Amino acid substitutions which can be expected not to essentially alter biological and immunological activities, have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information Lipman and Pearson developed a method for rapid and sensitive protein comparison (Science 227, 1435–1441, 1985) and determining the functional similarity between homologous polypeptides.

Functional derivatives which still show immunological activity towards the monoclonal antibody NKI-beteb or HMB-50 or HMB-45 are included within the scope of this invention.

Furthermore as functional derivatives of these peptides are also meant peptides derived from gp100 which are able to induce target cell lysis by tumor infiltrating lymphocytes.

In addition, with functional derivatives of these peptides are also meant addition salts of the peptides, amides of the peptides and specifically the C-terminal amides, esters and specifically the C-terminal esters and N-acyl derivatives specifically N-terminal acyl derivatives and N-acetyl derivatives.

The polypeptides according to the invention can be produced either synthetically or by recombinant DNA technology. Methods for producing synthetic polypeptides are well known in the art.

The organic chemical methods for peptide synthesis are considered to include the coupling of the required amino acids by means of a condensation reaction, either in homogenous phase or with the aid of a so-called solid phase. The condensation reaction can be carried out as follows:

a) condensation of a compound (amino acid, peptide) with a free carboxyl group and protected other reactive groups with a compound (amino acid, peptide) with a free amino group and protected other reactive groups, in the presence of a condensation agent;

b) condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1–3 (Ed. Gross, E. and Meienhofer, J.) 1979, 1980, 1981 (Academic Press, Inc.).

Production of polypeptides by recombinant DNA techniques is a general method which is known, but which has a lot of possibilities all leading to somewhat different results. The polypeptide to be expressed is coded for by a DNA sequence or more accurately by a nucleic acid sequence.

It has been found that the amino acid sequence of gp100 closely resembles the amino acid sequence of the already known melanoma-associated peptide pMel17, disclosed in Kwon, B. S. (1991).

The amino acid differences between gp100 and Pmel17 consist of substitutions at amino acid position 274 (T-C/PRO-LEU) and 597 (C-G/ARG-PRO) and a stretch of 7 amino acid absent in gp100 at position 587. A single nucleotide difference at position 762 (C-T) does not result in an amino acid substitution. Gp100 is also 80% homologous to a putative protein deduced from a partial cDNA clone (RPE-1) isolated from a bovine retinal cDNA library (Kim, R. Y. and Wistow, G. J., 1992) and 42% homologous to a chicken melanosomal matrix protein, MMP115 (Mochii, M., 1991). See also FIG. 2.

Also part of the invention is the nucleic acid sequence comprising the sequence encoding the gp100 polypeptide.

Preferably the sequence encoding gp100 is the sequence of SEQ ID NO:1.

As is well known in the art, the degeneracy of the genetic code permits substitution of bases in a codon resulting in another codon still coding for the same amino acid, e.g. the codon for the amino acid glutamic acid is both GAT and GAA. Consequently, it is clear that for the expression of a polypeptide with an amino acid sequence shown in SEQ ID NO:2 use can be made of a derivate nucleic acid sequence with such an alternative codon composition thereby differing from the nucleic acid sequence shown in SEQ ID NO:1.

"Nucleotide sequence" as used herein refers to a polymeric form of nucleotides of any length, both to ribonucleic acid (RNA) seqeuences and to desoxyribonucleic acid (DNA) seqeuences. In principle this term refers to the primary structure of the molecule. Thus, this term includes double and single stranded DNA, as well as double and single stranded RNA, and modifications thereof.

The nucleotide sequence of gp100 contains 2115 base pairs (bp) and terminates with a poly (A) tract of 15 nucleotides which is preceded by the consensus polyadenylation sequence AATAAA SEQ. ID. NO. 31. An open reading frame (ORF) extending from nucleotide 22 through 2007 is present in gp100 DNA. This ORF starts with an ATG codon within the appropriate sequence context for translation initiation and codes for a protein of 661 amino acids. The amino-terminal 20 amino acids fit all criteria for signal sequences, including a potential cleavage site after ALA at position 20 (−1), which would indicate that mature gp100 contains 641 amino acids (approximately 70 kD).

The most striking difference between gp100 and Pmel17 cDNAs is the inframe deletion of 21 bp in gp100 cDNA (FIG. 2). Comparison of the nucleotide sequence of genomic DNA with the sequence of gp100 cDNA revealed the presence of an intron (102 bp) just at the position of the 21 bp insertion in Pmel17 cDNA. The exon/intron boundaries nicely fit the consensus 5' donor and 3' acceptor splice site sequences (Padgett, 1986). In the genomic DNA, the sequence comprising the additional 21 bp in Pmel17 cDNA is located directly upstream of the 3' cleavage site used to generate gp100 RNA and is preceded by an alternative 3' acceptor splice site. Whereas the gp100-specific 3' acceptor splice site fits the consensus sequence, the Pmel17-specific 3' acceptor splice site appears to be sub-optimal in that it lacks a pyrimidine-rich region. Sub-optimal RNA processing sites are present in many alternatively processed messenger RNA precursors and have been implicated to function in regulation of alternative RNA processing (reviewed by Green, M. R., 1991). Collectively, these data prove that the transcripts corresponding to gp100 and Pmel17 cDNAs are generated by alternative splicing of a single primary transcript.

A further part of the invention are peptides, which are immunogenic fragments of the gp100 polypeptide.

Immunogenic fragments are fragments of the gp100 molecule, which still have the ability to induce an immunogenic response, i.e. that it is either possible to evoke antibodies recognizing the fragments specifically, or that it is possible to find T lymphocytes which have been activated by the fragments.

As has been said above it has been known that the immunogenic action of tumor associated antigens is often elicited through a T cell activating mechanism (Townsend, A. R. M. and Bodmer, H., Ann. Rev. Immunol. 7, 601–624, 1989). Cytotoxic T lymphocytes (CTLs) recognizing melanoma cells in a T cell receptor (TCR)-dependent and MHC-restricted manner have been isolated from tumor-bearing patients (reviewed by Knuth, A., 1992). Brichard et al. (1993) have shown that a peptide derived from tyrosinase, an other melanocyte-specific antigen, is recognized by a CTL clone.

It is known that the activation of T cells through the MHC molecule necessitates processing of the antigen of which short pieces (for example 8–12 mers) are presented to the T lymphocyte.

The immunogenic oligopeptides located in the gp100 sequence form also part of the invention.

We have found immunogenic peptide sequences of the gp100 sequence which are not only able to bind with the MHC I molecule, but which also have been demonstrated to recognize tumor infiltrating lymphocytes which have been isolated from a melanoma patient.

Several peptides have been found: the peptides having the amino acid sequences V-L-P-D-G-Q-V-I-W-V (SEQ ID NO:5), M-L-G-T-H-T-M-E-V (SEQ ID NO:24), R-L-M-K-Q-D-F-S-V (SEQ ID NO:25), (V)-(W)-(K)-T-W-G-Q-Y-W-Q-V-(L) (SEQ ID NO:10) and L-L-D-G-T-A-T-L-R-L (SEQ ID NO:4) have been found to bind to the MHC HLA-A2.1 molecule. In addition, the latter two peptides are recognized by anti-melanoma cytotoxic T lymphocytes in the context of HLA-A2.1.

Preferably these peptides are flanked by non-related sequences, i.e. sequences with which they are not connected in nature, because it has been found that such flanking enhances the immunogenic properties of these peptides, probably through a better processing and presentation by APC's.

Another part of the invention is formed by nucleotide sequences comprising the nucleotide sequences coding for the above mentioned peptides.

Next to the use of these sequences for the production of the peptides with recombinant DNA techniques, which will be exemplified further, the sequence information disclosed in the sequence listings for gp100 or its epitopes can be used for diagnostic purposes.

From these sequences primers can be derived as basis for a diagnostic test to detect gp100 or gp100-like proteins by a nucleic acid amplification technique for instance the polymerase chain reaction (PCR) or the nucleic acid sequence based amplification (NASBA) as described in U.S. Pat. No. 4,683,202 and EP 329,822, respectively.

With PCR large amounts of DNA are generated by treating a target DNA sequence with oligonucleotide primers such that a primer extension product is synthesized which is separated from the template using heat denaturation and in turn serves as a template, resulting in amplification of the target sequence. When RNA is to be amplified with PCR the RNA strand is first transcribed into a DNA strand with the aid of reverse transcriptase.

With the aid of NASBA large amounts of single stranded RNA are generated from either single stranded RNA or DNA or double stranded DNA. When RNA is to be amplified the ssRNA serves as a template for the synthesis of a first DNA strand by elongation of a first primer containing a ssRNA polymerase recognition site. The formed DNA strand in turn serves as the template for the synthesis of a second, complementary, DNA strand by elongation of a second primer, resulting in a double stranded active RNA-polymerase promoter site, and the second DNA serves as a template for synthesis of large amounts of the first template, the ssRNA, with the aid of RNA polymerase.

Detection of the amplified nucleotide sequence is established by hybridizing a complementary detection probe to the amplified nucleic acid. This probe can be labelled and/or immobilized on a solid phase.

Detection of the label can be performed through methods known in the art. Detection of nucleic acids bound through the probe to the solid phase can be done by compounds capable of selective detection of nucleic acids.

As said before the nucleotide sequences can be used for the production of gp100 or one of its epitopes with recombinant DNA techniques. For this the nucleotide sequence must be comprised in a cloning vehicle which can be used to transform or transfect a suitable host cell.

A wide variety of host cell and cloning vehicle combinations may be usefully employed in cloning the nucleic acid sequence. For example, useful cloning vehicles may include chromosomal, non-chromosomal and synthetic DNA sequences such as various known bacterial plasmids, and wider host range plasmids such as pBR 322, the various pUC, POEM and pBluescript plasmids, bacteriophages, e.g. lambda-gt-Wes, Charon 28 and the M13 derived phages and vectors derived from combinations of plasmids and phage or virus DNA, such as SV40, adenovirus or polyoma virus DNA (see also Rodriquez, R. L. and Denhardt (1988); Lenstra, 1990).

Useful hosts may include bacterial hosts, yeasts and other fungi, plant or animal hosts, such as Chinese Hamster Overy (CHO) cells or monkey cells and other hosts.

Vehicles for use in expression of the peptides will further comprise control sequences operably linked to the nucleic acid sequence coding for the peptide. Such control sequences generally comprise a promoter sequence and sequences which regulate and/or enhance expression levels. Furthermore an origin of replication and/or a dominant selection marker are often present in such vehicles. Of course control and other sequences can vary depending on the host cell selected.

Techniques for transforming or transfecting host cells are quite known in the art (see, for instance, Maniatis et al., 1982 and 1989).

It is extremely practical if, next to the information for the peptide, also the host cell is co-transformed or co-transfected with a vector which carries the information for an MHC molecule to which said peptide is known to bind. Preferably the MHC molecule is HLA-A2.1, HLA-A1 or HLA-A3.1, or any other HLA allele which is known to be present in melanoma patients. HLA-A2.1 is especially preferred because it has been established (Anichini A., 1993) that melanoma cells carry antigens recognized by HLA-A2.1 restricted cytotoxic T cell clones from melanoma patients.

Host cells especially suited for the expression of gp100 are the murine EL4 and P8.15 cells. For expression of gp100 human BLM cells (described by Katano, M., 1984) are especially suited because they already are able to express the MHC molecule HLA-A2.1.

Gp100 or any of its peptides or their nucleotide sequences mentioned above can be used in a vaccine for the treatment of melanoma.

In addition to an immunogenically effective amount of the active peptide the vaccine may contain a pharmaceutically acceptable carrier or diluent.

The immunogenicity of the peptides of the invention, especially the oligopeptides, can be enhanced by cross-linking or by coupling to an immunogenic carrier molecule (i.e. a macromolecule having the property of independently eliciting an immunological response in a patient, to which the peptides of the invention can be covalently linked).

Covalent coupling to the carrier molecule can be carried out using methods well known in the art, the exact choice of which will be dictated by the nature of the carrier molecule used. When the immunogenic carrier molecule is a protein, the peptides of the invention can be coupled, e.g. using water soluble carbodiimides such as dicyclohexylcarbodiimide, or glutaraldehyde.

Coupling agents such as these can also be used to cross-link the peptides to themselves without the use of a separate carrier molecule. Such cross-linking into polypeptides or peptide aggregates can also increase immunogenicity.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

Optionally, one or more compounds having adjuvant activity may be added to the vaccine. Suitable adjuvants are for example aluminium hydroxide, phosphate or oxide, oil-emulsions (e.g. of Bayol F(R) or Marcol 52(R)), saponins or vitamin-E solubilisate.

The vaccine according to the present invention can be given inter alia intravenously, intraperitoneally, intranasally, intradermally, subcutaneously or intramuscularly.

The useful effective amount to be administered will vary depending on the age and weight of the patient and mode of administration of the vaccine.

The vaccine can be employed to specifically obtain a T cell response, but it is also possible that a B cell response is elicited after vaccination. If so, the B cell response leads to the formation of antibodies against the peptide of the vaccine, which antibodies will be directed to the source of the antigen production, i.e. the tumor cells. This is an advantageous feature, because in this way the tumor cells are combatted by responses of both immunological systems.

Both immunological systems will even be more effectively triggered when the vaccine comprises the peptides as presented in an MHC molecule by an antigen presenting cell (APC). Antigen presentation can be achieved by using monocytes, macrophages, interdigitating cells, Langerhans cells and especially dendritic cells, loaded with one of the peptides of the invention. Loading of the APC's can be accomplished by bringing the peptides of the invention into or in the neighbourhood of the APC, but it is more preferable to let the APC process the complete gp100 antigen. In this way a presentation is achieved which mimicks the in vivo situation the most realistic. Furthermore the MHC used by the cell is of the type which is suited to present the epitope.

An overall advantage of using APC's for the presentation of the epitopes is the choice of APC cell that is used in this respect. It is known from different types of APC's that there are stimulating APC's and inhibiting APC's.

Preferred are the listed cell types, which are so-called 'professional' antigen presenting cells, characterized in that they have co-stimulating molecules, which have an important function in the process of antigen presentation. Such co-stimulating molecules are, for example, B7, CTLA-4, CD70 or heat stable antigen (Schwartz, 1992).

Fibroblasts, which have also been shown to be able to act as an antigen presenting cell, lacks these co-stimulating molecules.

It is also possible to use cells already transfected with a cloning vehicle harbouring the information for gp100 and which are cotransfected with a cloning vehicle which comprises the nucleotide sequence for an MHC class I molecule, for instance the sequence coding for HLA A2.1, HLA A1 or HLA A3.1. These cells will act as an antigen presenting cell and will present gp100-fragments in the MHC class I molecules which are expressed on their surface. It is envisaged that this presentation will be enhanced, when the cell is also capable of expressing one of the above-mentioned co-stimulating molecules, or a molecule with a similar function. This expression can be the result of transformation or transfection of the cell with a third cloning vehicle having the sequence information coding for such a co-stimulating molecule, but it can also be that the cell already was capable of production of co-stimulating molecules.

In stead of a vaccine with these cells, which next to the desired expression products, also harbour many elements which are also expressed and which can negatively affect the desired immunogenic reaction of the cell, it is also possible that a vaccine is composed with liposomes which expose MHC molecules loaded with peptides, and which, for instance, are filled with lymphokines. Such liposomes will trigger a immunologic T cell reaction.

By presenting the peptide in the same way as it is also presented in vivo an enhanced T cell response will be evoked. Furthermore, by the natural adjuvant working of the, relatively large, antigen presenting cells also a B cell response is triggered. This B cell response will a.o. lead to the formation of antibodies directed to the peptide-MHC complex. This complex is especially found in tumor cells, where it has been shown that in the patient epitopes of gp100 are presented naturally, which are thus able to elicit a T cell response. It is this naturally occurring phenomenon which is enlarged by the vaccination of APC's already presenting the peptides of the invention. By enlarging not only an enlarged T cell response will be evoked, but also a B cell response which leads to antibodies directed to the MHC-peptide complex will be initiated.

The vaccines according to the invention can be enriched by numerous compounds which have an enhancing effect on the initiation and the maintenance of both the T cell and the B cell response after vaccination.

In this way addition of cytokines to the vaccine will enhance the T cell response. Suitable cytokines are for instance interleukines, such as IL-2, IL-4, IL-7, or IL-12, GM-CSF, RANTES, tumor necrosis factor and interferons, such as IFN-.

In a similar way antibodies against T cell surface antigens, such as CD2, CD3, CD27 and CD28 will enhance the immunogenic reaction.

Also the addition of helper epitopes to stimulate $CD4^+$ helper cells or $CD8^+$ killer cells augments the immunogenic reaction. Alternatively also helper epitopes from other antigens can be used, for instance from heat shock derived proteins or cholera toxin.

Another part of the invention is formed by usage of gp100 reactive tumor infiltrating lymphocytes (TIL's). In this method the first step is taking a sample from a patient. This is usually done by resection of a tumor deposit under local anaesthesia. The TIL's present in this specimen are then expanded in culture for four to eight weeks, according to known methods (Topalian, S. L. et al., 1987). During this culture the TIL's are then checked for reactivity with gp100 or one of the epitopes derived from gp100. The TIL's which recognize the antigen are isolated and cultured further.

The tumor infiltrating lymphocytes, reactive with gp100, which are obtained through this method, form also of the invention. One such TIL cell line, designated TIL 1200, has been found which specifically reacts with gp100 and its epitopes. This TIL 1200 cell line also expresses the MHC molecule HLA-A2.1. Furthermore expression of TCR $\alpha/\beta$, CD3 and CD8 by this cell line has been demonstrated. Furthermore TIL 1200 recognizes transfectants expressing both HLA-A2.1 and gp100.

This TIL 1200 and other TIL's recognizing gp100 are suited for treatment of melanoma patients. For such treatment TIL's are cultured as stated above, and they are given back to the patients by an intravenous infusion. The success of treatment can be enhanced by pre-treatment of the tumor bearing host with either total body radiation or treatment with cyclophosphamide and by the simultaneous administration of interleukin-2 (Rosenberg, S. A. et al., 1986).

The TIL's infused back to the patient are preferably autologous TIL's (i.e. derived from the patient's own tumor) but also infusion with allogenic TIL's can be imagined.

A further use of the TIL's obtained by the method as described above is for in vivo diagnosis. Labelling of the TIL's, for instance with $^{111}$In (Fisher, 1989) or any other suitable diagnostic marker, renders them suited for identification of tumor deposits in melanoma patients.

Another part of the invention is formed by the T cell receptor (TCR) expressed by gp100 reactive CTLs. As is well known in the art, the TCR determines the specificity of a CTL. Therefore, the cDNA encoding the TCR, especially its variable region, can be isolated and introduced into T cells, hereby transferring anti-tumor activity to any T cell. Especially introduction of such a TCR into autologous T cells and subsequent expansion of these T cells, will result in large numbers of CTL suitable for adoptive transfer into the autologous patient.

Also cells harbouring this T cell receptor can be used for vaccination purposes.

A vaccine can also be composed from melanoma cells capable of expression of gp100. It is possible to isolate these cells from a patient, using anti-gp100 antibodies, such as NKI-beteb, but is also possible to produce such melanoma cells from cultured melanoma cell lines, which either are natural gp100-producers or have been manipulated genetically to produce gp100. These cells can be irradiated to be non-tumorogenic and infused (back) into the patient. To enhance the immunologic effect of these melanoma cells it is preferred to alter them genetically to produce a lymphokine, preferably interleukine-2 (IL-2) or granulocyte-macrophage colony stimulation factor (GM-CSF). Gp100$^+$ melanoma cells can be transfected with a cloning vehicle having the sequence coding for the production of IL-2 or GM-CSF.

Infusion of such a vaccine into a patient will stimulate the formation of CTL's.

Another type of vaccination having a similar effect is the vaccination with pure DNA, for instance the DNA of a vector or a vector virus having the DNA sequence encoding the gp100 antigen or peptides derived therefrom. Once injected the virus will infect or the DNA will be transformed to cells which express the antigen or the peptide(s).

Antibodies to any gp100 peptide, including antibodies to (V)-(W)-(K)-T-W-G-Q-Y-W-Q-V-(L) SEQ ID NO:10, and L-L-D-G-T-A-T-L-R-L SEQ ID NO:4, are also part of the invention.

Monospecific antibodies to these peptides can be obtained by affinity purification from polyspecific antisera by a modification of the method of Hall, R. et al. (1984). Polyspecific antisera can be obtained by immunizing rabbits according to standard immunisation schemes.

Monospecific antibody as used herein is defined as a single antibody species or multiple antibody species with homogeneous binding characteristics for the relevant antigen. Homogeneous binding as used herein refers to the ability of the antibody species to bind to ligand binding domain of the invention.

The antibody is preferably a monoclonal antibody, more preferably a humanised monoclonal antibody.

Monoclonal antibodies can be prepared by immunizing inbred mice, preferably Balb/c with the appropriate protein by techniques known in the art (Köhler, G. and Milstein C., 1975). Hybridoma cells are subsequently selected by growth in hypoxanthine, thymidine and aminopterin in an appropriate cell culture medium such as Dulbecco's modified Eagle's medium (DMEM). Antibody producing hybridomas are cloned, preferably using the soft agar technique of MacPherson (1973). Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific anti-monoclonal antibodies are produced by cultivating the hybridomas in vitro or preparing ascites fluid in mice following hybridoma injection by procedures known in the art.

It is preferred to use humanized antibodies. Methods for humanizing antibodies, such as CDR-grafting, are known (Jones, P. T. et al., 1986). Another possibility to avoid antigenic response to antibodies reactive with polypeptides according to the invention is the use of human antibodies or fragments or derivatives thereof.

Human antibodies can be produced by in vitro stimulation of isolated B-lymphocytes, or they can be isolated from (immortalized) B-lymphocytes which have been harvested from a human being immunized with at least one ligand binding domain according to the invention.

Antibodies as described above can be used for the passive vaccination of melanoma patients. A preferred type of antibodies for this kind of vaccine are antibodies directed against the above-mentioned peptides presented in connection with the MHC molecule. To produce these kind of antibodies immunization of peptides presented by APC's is required. Such an immunization can be performed as described above. Alternatively, human antibodies to peptide-MHC complexes can be isolated from patients treated with a vaccine consisting of APC's loaded with one of said peptides.

The antibodies, which are formed after treatment with one of the vaccines of the invention can also be used for the monitoring of said vaccination. For such a method serum of the patients is obtained and the antibodies directed to the peptide with which has been vaccinated are detected. Knowing the antibody titre from this detection it can be judged if there is need for a boost vaccination.

Specific detection of said antibodies in the serum can be achieved by labelled peptides. The label can be any diagnostic marker known in the field of in vitro diagnosis, but most preferred (and widely used) are enzymes, dyes, metals and radionuclides, such as $^{67}$Ga, $^{99m}$Tc, $^{111}$In, $^{113m}$In, $^{123}$I, $^{125}$I or $^{131}$I.

The radiodiagnostic markers can be coupled directly to the peptides of the invention or through chelating moieties which have been coupled to the peptide directly or through linker or spacer molecules. The technique of coupling of radionuclides to peptides or peptide-like structures is already known in the field of (tumor) diagnostics from the numerous applications of labelled antibodies used both in in vivo and in in vitro tests.

Direct labelling of peptides can for instance be performed as described in the one-vial method (Haisma, 1986). A general method for labelling of peptides through chelators, with or without linker or spacer molecules, has for instance been described in U.S. Pat. Nos. 4,472,509 and 4,485,086. Chelators using a bicyclic anhydride of DTPA have been disclosed in Hnatowich, D. J. et al. (1983). Coupling through diamide dimercaptide compounds has been disclosed in EP 188,256.

BRIEF DESCRIPTION OF THE FIGURES

The present invention is further described by way of example with reference to the accompanying figures, in which:

FIG. 1 shows the genomic organization of part of the human gp100/Pmel17 gene. A (SEQ ID NO:33) and A' (SEQ ID NO:34) represent the introns which are removed in transcripts corresponding to gp100 cDNA and Pmel17 cDNA respectively. Exon sequences are indicated in capitals and intron sequences as small letters. The best fit to the branch point sequence (Ruskin B. et al., 1984) is underlied.

FIG. 2 shows an alignment of the carboxyterminal part of members of the gp100 (SEQ ID NO:2)/Pmel17 family. Identical amino acids (–) and gaps (*) are indicated. Conserved cysteine residues (#) are indicated as well.

Figure 3:
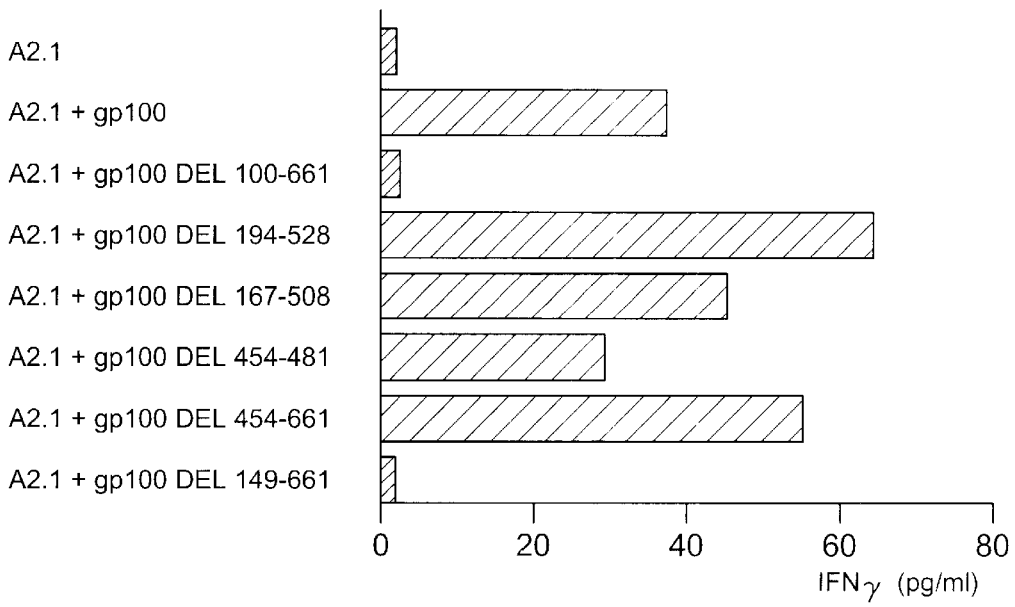
FIG. 3. (A) Gp100 deletion mutants encoding parts of the gp100 protein are shown (numbers indicate amino acids in the gp100 protein as indicated in SEQ ID NO:2).

(B) Recognition by TIL 1200 of cells transfected with HLA-A2.1 and the gp100 deletion mutants shown in FIG. 3A.

FIG. 4 (A) Five peptides derived from the gp110 148–166 region (SEQ ID NO:20, SEQ ID NO:21, SEQ ID NO:22, SEQ ID NO:23, SEQ ID NO:8, SEQ ID NO:4 and residues 280–288 of SEQ ID NO:2, respectively), varying from an 8-mer to 11-mer, were tested for recognition by TIL 1200. Specific lysis was detected at an effector to target ratio of 30:1.

(B) Titration of gp100 peptides (SEQ ID NO:20, SEQ ID NO:21, SEQ ID NO:22, SEQ ID NO:23, and SEQ ID NO:8, respectively) identified in FIG. 4A for recognition by TIL 1200 (E/T ratio 30:1).

Figure 5:
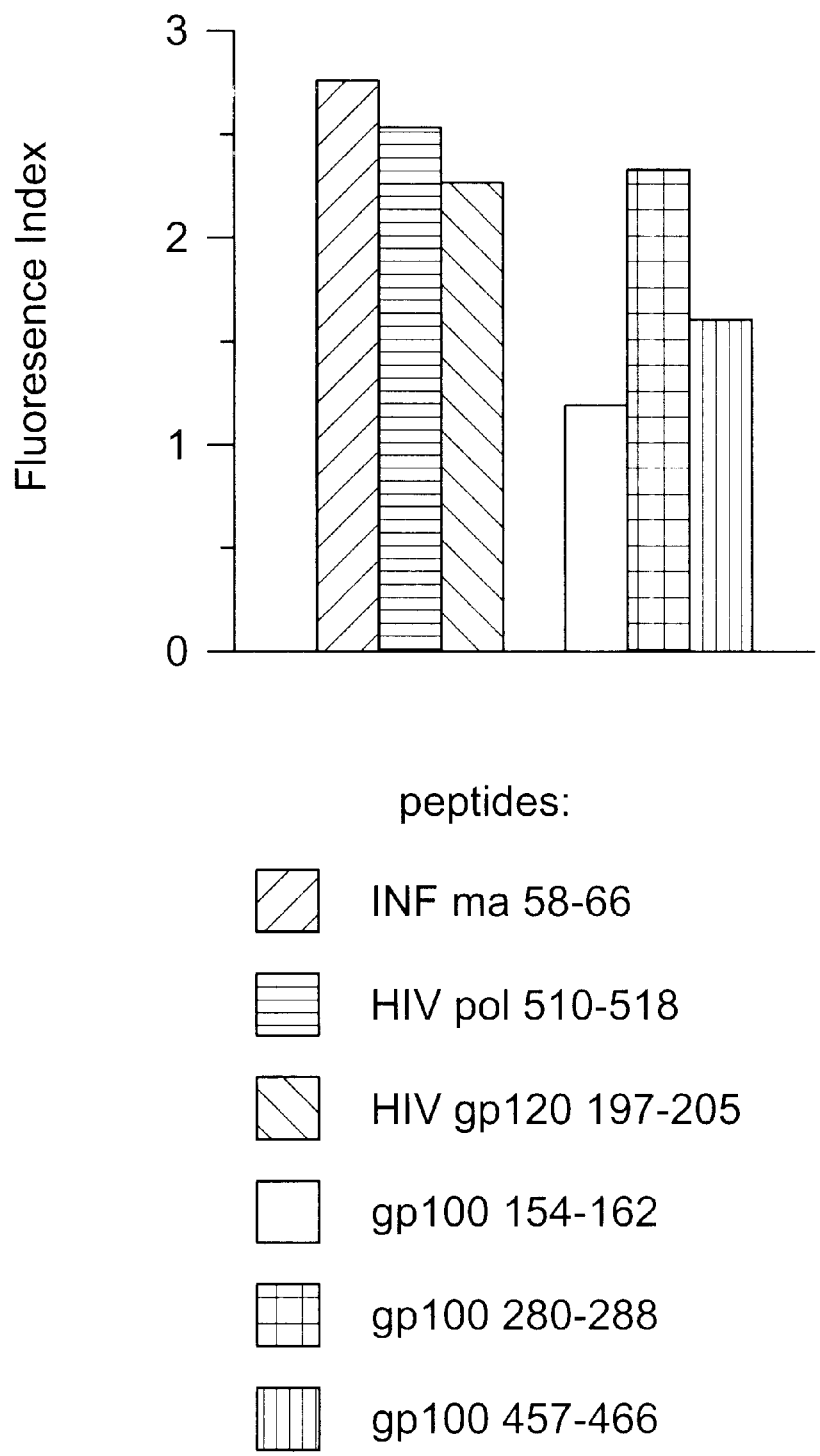

FIG. 5. Binding of gp100 and viral epitopes to HLA A2.1.

DETAILED DESCRIPTION OF THE INVENTION

EXAMPLE 1

Molecular Characterization of GP100

MATERIALS AND METHODS

Cells and monoclonal antibodies

The melanoma cell lines Mel-2a, M14, MEWO, BLM (Vennegoor et al., 1988; van Muijen et al., 1991; Bean et al., 1975; Katano et al., 1984) and the uveal melanoma cell line Mel 202 (Ksander et al., 1991) have been previously described. Isolation of normal human melanocytes from breast or foreskin was performed by the method of Eisinger and Marko (1982) with modifications by (Smit et al., 1993).

Mabs NKI-beteb and HMB-50 have been described previously (Vennegoor et al., 1988; Vogel and Esclamado, 1988). MAb HMB-45 was purchased from Enzo Biochem.

DNA constructs and transfections

The 2.2 kb Eco RI fragment containing gp100 cDNA was blunt-ended by filling in the ends with Klenow DNA Polymerase and then cloned in both orientations (pSVLgp100+ and pSVLgp100–) in the Sma I site of the eukaryotic expression vector pSVL (Pharmacia). pSVL contains the SV40 late promoter and polyadenylation site as well as the SV40 origin of replication, allowing a very high copy number during transient expression in COS-7 cells.

For the construction of the 3' truncated gp100 transcription unit pSVLgp100+(@BS) we deleted the sequence between the Bgl II site in the 3' part of gp100 cDNA and the Sac I site in the multiple cloning site of the vector. The resulting construct encodes a truncated gp100 protein in which the carboxy-terminal 133 amino acids of gp100 are replaced by 4 amino acids (Arg-Ile-Gln-Thr) SEQ. ID. NO. 32 encoded by vector sequences.

Transient expression of the constructs in COS-7 cells was performed by using 40 μg/ml lipofectin reagent from BRL (Felgner et al., 1987) and 7.5 μg DNA as described previously (Loenen et al., 1991).

Immunofluorescence

Transfected COS-7 cells were prepared for immunofluorescence 48 hours after the addition of the lipofectin/DNA mixture as described previously (Vennegoor et al., 1988). After incubation with the primary antibody for 45 minutes, cells were washed and incubated with fluorescein isothiocyanate (FITC)-labeled goat F(ab)'$_2$ anti-mouse IgG (Nordic) for 30 minutes. Preparations were examined using a confocal laser scanning microscope at 488 nm (Biorad MRC 600).

Metabolic labeling, Immunoprecipitations and V8 protease mapping.

Immunoprecipitation experiments were performed on metabolically labeled (L-[$^{35}$S]-methionine/cysteine;

Amersham) cells as described by Vennegoor et al. (1988) using either mAb NKI-beteb or HMB-50 covalently linked to protein A-CL 4B sepharose beads (Pharmacia). In some experiments tunicamycin (75 µg/ml, Calbiochem) was added during the pre-labeling period and remained present during the metabolic labeling reaction (12.5 minutes). Immunoprecipitates were analyzed under reducing conditions (5% β-mercaptoethanol in SDS-sample buffer) by SDS-PAGE using 5–17.5% polyacrylamide gradient gels. The relative molecular weight of the proteins was determined using co-electrophorised, pre-stained molecular weight markers (BRL). Gels were treated with 1 M sodium salicylate (pH 5.4) prior to autoradiography (Kodak XAR).

V8 protease mapping was performed using the digestion for proteins in gel slices procedure described by Cleveland et al. (1977). Briefly, gel slices containing the 100 kD proteins were placed in the wells of a second SDS-gel (10%) and overlayed with Staphylococcus aureus V8 protease (2.5 µg/sample, Miles laboratories). After electrophoresis gels were treated as described above.

Molecular cloning of part of the gp100/Pmel17 gene.

Part of the gp100/Pmel17 gene was amplified by PCR (Taq DNA Polymerase was from Gibco) on human genomic DNA isolated from peripheral blood lymphocytes (PBL's) using the following primers: 1497/1516: 5'-TATTG-AAAGTGCCGAGATCC-3' SEQ ID NO:26 and 1839/1857: 5'-TGCAAGGACCACAGCCATC-3' SEQ ID NO:27 as described previously (Adema and Baas, 1991). The PCR products were subsequently amplified using a nested set of primers containing an additional Eco RI site (5'-TATCTAGAATTCTGCACCAGATACTGAAG-3' SEQ ID NO:11 and 5'-TATCTAGAATTCTGCAAGATGCCCACG-ATCAG-3') SEQ ID NO:12. The underlined Eco RI sites in these primers were used to clone the PCR product in the Eco RI site of pUC 18.

RNA isolation and analysis

Total RNA was isolated using the guanidine thiocyanate procedure and centrifugation through a cushion of Cesium chloride (Chirgwin et al., 1979). cDNA was prepared using the Geneamp RNA PCR kit (Perkin Elmer Cetus) as indicated by the manufacturer. PCR analysis of the cDNAs was performed for 35 cycles in the presence of 3 mM MgCl$_2$ using primers 1497/1516 and 1839/1857 (see above) as described previously (Adema and Baas, 1991). The reaction products were size-fractionated on an agarose gel, blotted onto a nylon membrane (Hybond-N, Amersham) and hybridized to [$^{32}$P]-labeled oligonucleotide probes as described previously (Adema and Baas, 1991). As probes we used either a gp100-specific exon/exon junction oligonucleotide (5'-CTTCTTGACCAGGCATGATA-3') SEQ ID NO:19 or a Pmel17-specific oligonucleotide (5'-TGTGAGAAGAATCCCAGGCA-3') SEQ ID NO:14 which corresponds to 20 of the additional 21 nucleotides present in Pmel17 cDNA. In every hybridization experiment a spot blot containing an oligonucleotide comprising the Pmel17 exon/exon junction (5'-GCTTATCATG-CCTGTGCCTGGATTCTTCTCACAGGT-3') SEQ ID NO:15 was included as a control.

Nucleotide sequence analysis

Gp100 cDNA and genomic DNA clones were sequenced by the dideoxy-nucleotide sequencing method (Sanger et al., 1977) using T7 DNA polymerase (Pharmacia). The sequence of both strands was determined in each case. Since the genomic DNA clones were obtained after PCR, the sequence of four independent clones was determined. Analysis of the DNA sequence was performed using the University of Wisconsin Genetics Computing Group sequence analysis programs (Devereux et al., 1984).

Results

Expression of gp100 cDNA in non-pigmented COS-7 cells results in immunoreactivity with mAbs NKI-beteb, HMB-50 and HMB-45.

Expression of gp100 cDNA in gp100-negative BLM melanoma cells results in immunoreactivity with the melanocyte lineage-specific mAbs, NKI-beteb, HMB-50 and HMB-45. To determine whether expression of gp100-c1 cDNA in non-melanocytic cells also results in immunoreactivity with these mAbs, we performed transient expression experiments in COS-7 cells (monkey kidney fibroblasts) with constructs containing gp100 cDNA in the coding or non-coding orientation. Only COS-7 cells transfected with the construct containing the cDNA in the coding orientation (COS-7/pSVLgp100+) react with all three mAbs. These data demonstrate that immunoreactivity with mAbs NKI-beteb, HMB-50 and HMB-45 after expression of gp100 cDNA is not restricted to melanocytic cells. In addition, these data show that the COS expression system can be used for further biochemical characterization of the proteins encoded by gp100 cDNA.

Analysis of the proteins encoded by gp100 cDNA.

To characterize the proteins encoded by gp100 cDNA, COS-7/pSVLgp100+ cells were metabolically labeled and subjected to immunoprecipitation with mAb NKI-beteb or HMB-50. MoAbs NKI-beteb and HMB-50 specifically immunoprecipitate proteins of approximately 100 kD (95–110 kd) from extracts of COS-7/pSVLgp100+ cells. The molecular weight of these proteins is similar (see also below) to those immunoprecipitated from extracts of metabolically labeled MEWO cells which express the antigens endogenously (Vennegoor et al., 1988). Consistent with previous reports (Vennegoor et al., 1988; Vogel and Esclamado, 1988), both mAbs also recognize a protein of 10 kD in extracts of MEWO melanoma cells. A protein of the same size reacts with mAb NKI-beteb in COS-7/pSVLgp100+ cells and can be discerned with mAb HMB-50 after prolonged exposure (not shown). We note that the amount of the 10 kd protein varied considerably between experiments. No specific proteins are immunoprecipitated by either of the mAbs from extracts prepared from COS-7 cells transfected with the construct containing the DNA in the non-coding orientation.

Glycoproteins of approximately 100 kD reacting with mAbs NKI-beteb and HMB-50 have also been found in culture medium of melanoma cells (Vennegoor et al., 1988; Vogel and Esclamado, 1988). Comparison of the culture medium of metabolically labeled COS-7/pSVLgp100+ cells and MEWO cells reveals that both mAbs also recognize proteins of about 100 kD (see also below) in the culture medium of these cells. No proteins of 10 kD are immunoprecipitated by the mAbs from the culture medium of COS-7/pSVLgp100+ cells, as has been shown for melanoma cells. These data demonstrate that, as in melanoma cells, the proteins of about 100 kd recognized by mAbs NKI-beteb and HMB-50 in COS-7/pSVLgp100+ cells are secreted.

To exclude the possibility that the proteins detected by the mAbs are derived from endogenous genes induced after transfection with gp100 cDNA, we performed immunoprecipitation experiments with COS-7 cells expressing a 3' truncated gp100 transcription unit (see Materials & Methods for details). Proteins of approximately 85 kd are immunoprecipitated by both mAbs from COS-7 cells expressing this construct, consistent with a deletion of 129 amino acids. This finding provides direct evidence that the 100 kd protein recognized by mAbs NKI-beteb and HMB-50 in COS-7/pSVLgp100+ cells is encoded by gp100 cDNA.

The 100 kd protein encoded by gp100 cDNA is identical to gp100

The proteins of about 100 kD identified by mAbs NKI-beteb and HMB-50 in COS-7/pSVLgp100+ cells versus MEWO cells have a slightly different mobility when analyzed by SDS-PAGE. Since the proteins reacting with these mAbs have been shown to be glycosylated in melanoma cells (Vennegoor et al., 1988; Vogel and Esclamado, 1988), these differences could be due to altered glycosylation, an event frequently observed in the COS expression system. To confirm this, mAb NKI-beteb was used to immunoprecipitate proteins from MEWO cells and COS-7/pSVLgp100+ cells cultured in the presence of the glycosylation inhibitor tunicamycin. In both COS-7/pSVLgp100+ cells and MEWO cells the size of the proteins of about 100 kd is reduced to two protein bands of 90 kd and 85 kD, confirming that the observed difference in mobility is due to altered glycosylation.

To provide further evidence that the proteins recognized by mAb NKI-beteb in COS-7/pSVLgp100+ cells and MEWO cells are identical, we performed a V8 protease mapping experiment. The same protein fragments are obtained after V8 protease digestion of the major 100 kD protein isolated from COS-7/pSVLgp100+ cells or MEWO cells. We conclude from these data that gp100 cDNA encodes the melanocyte lineage-specific glycoprotein gp100 recognized by mAbs NKI-beteb and HMB-50 in melanoma cells.

Gp100 is a type I transmembrane protein highly homologous to Pmel17

The nucleotide sequence of gp100 cDNA was determined. It contains 2115 base pairs (bp) and terminates with a poly(A) tract of 15 nucleotides which is preceded by the consensus polyadenylation sequence AATAAA SEQ. ID. NO:31 (Proudfoot and Brownlee, 1976). An open reading frame (ORF) extending from nucleotide 22 through 2007 is present in gp100 cDNA. This ORF starts with an ATG codon within the appropriate sequence context for translation initiation (Kozak, 1987) and codes for a protein of 661 amino acids (SEQ ID NO:1). The amino-terminal 20 amino acids fit all criteria for signal sequences, including a potential cleavage site after ALA at position 20 (von Heyne, 1986), which would indicate that mature gp100 contains 641 amino acids (approximately 70 kD). Based on hydrophobicity plot analysis (Kyte and Doolittle, 1982), a single transmembrane domain bordered by charged residues is present in the carboxy-terminal part (amino acids 591–611) of gp100. The predicted cytoplasmic domain is 45 amino-acids long. Five putative N-linked glycosylation sites are present, consistent with gp100 being a glycoprotein. Furthermore, a histidine-rich domain (amino acids 182–313), a threonine-rich domain (amino acids 309–427) containing repetitive amino acid sequences, and a cysteine-rich domain (475–566 amino acids) are present.

A data base search (Pearson and Lipman, 1988; Altschul et al., 1990) revealed that gp100 is almost identical to Pmel17, another melanocyte-specific protein (Kwon et al., 1991). The amino acid differences between gp100 and Pmel17 consist of substitutions at position 274 (T-C/PRO-LEU) and 597 (C-G/ARG-PRO) and a stretch of 7 amino acid absent in gp100 at position 587 (see also FIG. 2). A single nucleotide difference at position 782 (C-T) does not result in an amino acid substitution. Gp100 is also 80% homologous to a putative protein deduced from a partial cDNA clone (RPE-1) isolated from a bovine retinal cDNA library (Kim and Wistow, 1992) and 42% homologous to a chicken melanosomal matrix protein, MMP115 (Mochii et al., 1991).

Gp100 and Pmel17 are encoded by a single gene

The most striking difference between gp100 and Pmel17 cDNAs is the inframe deletion of 21 bp in gp100 cDNA. One possible explanation for this difference is the existence of two closely related genes. However, since both cDNAs have identical nucleotide sequences in their 3' untranslated regions this explanation is not likely. Another possibility is that both cDNAs correspond to transcripts generated by alternative splicing of a single primary transcript. To test this hypothesis, we used PCR to analyze the genomic DNA corresponding to the part of the gp100 gene surrounding the putative alternative splice site. Comparison of the nucleotide sequence of this genomic DNA with the sequence of gp100-c1 cDNA revealed the presence of an intron (102 bp) just at the position of the 21 bp insertion in Pmel17 cDNA (FIG. 1). The exon/intron boundaries nicely fit the consensus 5' donor and 3' acceptor splice site sequences (Padgett et al., 1986). In the genomic DNA, the sequence comprising the additional 21 bp in Pmel17 cDNA is located directly upstream of the 3' cleavage site used to generate gp100 RNA and is preceded by an alternative 3' acceptor splice site (FIG. 1). Whereas the gp100-specific 3' acceptor splice site fits the consensus sequence, the Pmel17-specific 3' acceptor splice site appears to be sub-optimal in that it lacks a pyrimidine-rich region (FIG. 1). Sub-optimal RNA processing sites are present in many alternatively processed messenger RNA precursors and have been implicated to function in regulation of alternative RNA processing (reviewed by Green, 1991). Collectively, these data prove that the transcripts corresponding to gp100 and Pmel17 cDNAs are generated by alternative splicing of a single primary transcript and thus originate from a single gene.

Expression of gp100 and Pmel17 RNAs in cells of the melanocytic lineage

The finding that gp100 and Pmel17 RNAs arise by alternative splicing of a single primary transcript, raises the question whether this occurs in a developmentally regulated manner. An RNA species of 2.5 kb is the major RNA product detected by gp100 cDNA on Northern blots containing RNA isolated from melanocytic cells. The same results were obtained by Kwon et al. (1987) using Pmel17-1 cDNA as a probe. However, neither of the probes discriminate between gp100 and Pmel17 RNAs. To investigate the expression of gp100 and Pmel17 RNAs in cells of the melanocytic lineage, we performed a reverse transcriptase/polymerase chain reaction (RT/PCR) assay followed by Southern blotting and hybridization to either a gp100 specific exon/exon junction- or a Pmel17-specific oligonucleotide probe (see Materials & Methods). Gp100 and Pmel17 spliced products are both detected in 3 out of 4 cutanous melanoma cells, in uveal melanoma cells as well as in neonatal and adult melanocytes. No products are detected with either probe in gp100-negative BLM melanoma cells. These results demonstrate that in all melanocytic cells examined, gp100 and Pmel17 RNAs are expressed simultaneously.

EXAMPLE 2

Recognition of GP100 by TIL's

MATERIAL AND METHODS

Cell culture

TIL's were generated by growth of single cell suspensions of metastatic melanomas with 1,000 U/ml IL-2 (Cetus Corp., Emeryville, Calif.) and were grown as described previously (Kawakami, 1992). Melanoma cell lines Mel 397 and Mel 624 were obtained and grown as reported previously (Kawakami, 1992). HLA-A2.1$^+$ melanoma cell lines MeWo (Bean, 1975) and BLM (Katano, 1984) and murine P815 transfectants were grown in DMEM (Gibco, Paisley, Scotland, UK) plus 7.5% heat inactivated FCS (Gibco). JY, K562, and murine EL4 transfectants were cultured in Iscoves medium (Gibco) plus 7.5% FCS. Murine cells were grown in the presence of $5 \cdot 10^5$ M β-ME, and all media contained antibiotics. Isolation of normal melanocytes from foreskin was performed by the method of Eisinger and Marko (1982) with modifications as described previously (Smit, 1989). Melanocytes from passages two to three were used in chromium release assays.

DNA Constructs and transfection.

Plasmid pBJ1gp100neo was obtained by cloning the EcoRI fragment of a lambda gp100 cDNA clone in the coding orientation in the polylinker pBJ1-neo (Lin, 1990). Plasmid pBA2 containing a genomic fragment encoding HLA-A2.1 and human β-2 microglobulin was kindly provided by E. J. Baas (The Netherlands Cancer Institute, Division of Biochemistry, Amsterdam, The Netherlands). Plasmid pGK-hyg contains the hygromycin phosphotransferase gene (Te Riele, 1990). For the introduction of the HLA-A2.1 and human β-2 microglobulin genes, EL4 cells were transfected with 18 μg of pBA2 and 2 μg of pGK-hyg DNA according to the calcium phosphate coprecipitation procedure (Graham, 1973) using Calciumphosphate Transfection Systems (Gibco BRL, Gaithersburg, Md.). 24 h after transfection, 500 μg/ml hygromycin B (Calbiochem-Novabiochem Corp., La Jolla, Calif.) was added to the medium for the selection of stable transfectants. HLA-A2.1$^+$ gp100$^+$ EL4 cells were obtained by transfection of stable HLA-A2.1$^+$ EL4 clones with 20 μg of pBJ1-gp100neo DNA by calcium phosphate coprecipitation and were selected with 1 mg/ml G418. P815 A2.1 and P815 A2.1/gp100 cells were kindly provided by P. Coulie (Ludwig Ins., Brussels, Belgium).

mAb and flow cytometry

Phenotypic analysis of melanomas, transfectants, and normal melanocytes was performed by indirect immunofluorescence followed by flow cytometry using a FACScan$^R$ (Becton Dickinson & Co., Mountain View, Calif.). Purified anti-gp100 mAb NKI-beteb (Vennegoor, 1988) and anti-HLA-A2 mAbs BB7.2 (culture supernatant; Parham, 1981) and MA2.1 (ascites 1:500 dilution; Parham, 1978) were used as primary reagents. FITC conjugated GAM-IgG-F(ab')$_2$ (Zymed Laboratories, Inc. S. San Francisco, Calif.) was used for the second incubation. For the detection of the intracellular gp100 antigen cells were permeabilized in 0.01% digitonin and were subsequently fixed in 1% paraformaldehyde.

Chromium Release Assay

Chromium Release assays were performed as described previously (Kawakami, 1992). Briefly, $10^6$ target cells were incubated with 100 μCi Na$^{51}$CrO$_4$ (Amersham Int., Bucks, UK) for 1 hour. Various amounts of effector cells were then added to $2 \cdot 10^3$ target cells in triplicate wells of U-bottomed microtiter plates (Costar, Badhoevedorp, The Netherlands) in a final volume of 150 μl. After 5 hours of incubation, part of the supernatant was harvested and its radioactive content measured. Target cells were incubated for 48 hours with 50 U/ml human (Boehringer, Ingelheim, Germany) or mouse recombinant IFN- (TNO, Rijswijk, The Netherlands) before use in chromium release assays.

TIL 1200

In search of gp-100 specific cytotoxic T lymphocytes (CTLs) we focused on HLA-A2.1 as a restriction element because of its widespread occurrence in Caucasians and its presumptive dominant role in CTL reactivity against melanoma. A HLA-A2.1$^+$ TIL line, TIL 1200 (Shilyansky, J. et al, 1994), was used for this study. This TIL line expresses TCR α/β, CD3 and CD8.

Results

HLA-A2.1-restricted killing of melanoma tumor cells by TIL 1200 corresponds to gp100 expression.

Cytolytic activity of TIL 1200 was analyzed using a panel of human melanoma cell lines. TIL 1200 efficiently lysed HLA-A2.1$^+$ Mel 624 and MeWo melanoma tumor cells, which both express gp100, whereas no reactivity towards HLA-A2.1$^-$ gp100$^+$ Mel 397 cells was seen. It is interesting to note that we observed that HLA-A2.1$^+$ BLM melanoma cells are also resistant to lysis by TIL 1200. Furthermore, HLA-A2.1$^+$ EBV-transformed B cells (JY), which also lack gp100 expression, and K562 cells, were not lysed by TIL 1200. Together, these data demonstrate that TIL 1200 displays HLA-A2.1-restricted killing which correlates with gp100 expression.

TIL 1200 recognizes HLA-A2.1$^+$ gp100$^+$ transfectants.

EL4 cells cotransfected with a genomic fragment encoding HLA-A2.1 together with a plasmid conferring hygromycine resistance were selected and analyzed by flow cytometry. HLA-A2.1 expressing cells were subsequently transfected with pBJ1-gp100neo, which encodes gp100 and confers resistance to G418. Stable transfectants were selected and were screened for gp100 expression using mAb NKI/beteb. In collaboration with P. Coulie a similar panel of transfectants was generated in murine P815 cells (P815 A2.1 and p815 A2.1/gp100). Using these murine transfectants as target cells in chromium release assay, we clearly observed gp100 specific lysis by TIL 1200. The percent specific lysis (25–35%, E/T 30:1) of murine EL4 A2.1/gp100 and P815 A2.1/gp100 transfectants by TIL 1200 was somewhat lower compared with that observed with HLA-A2.1$^+$ gp100$^+$ human melanoma cells (45–60%, E/T 30:1). This difference may be explained by nonmatched accessory molecules between human TIL's and murine transfectants. To overcome this we introduced the gp100 antigen into human HLA-A2.1$^+$ gp100$^-$ BLM melanoma cells by transfection of pBJ1-gp100neo. Stable BLM gp100 clones were tested in chromium release assays using TIL 1200. BLM gp100 clones proved to be as sensitive to lysis by TIL 1200 as Mel 624 and MeWo cells which express the gp100 antigen endogenously. The gp100 specificity of TIL 1200 was further demonstrated by the absence of lysis of G418-resistant BLM cells not expressing gp100, excluding the possibility that neomycin-derived peptides are recognized.

EXAMPLE 3

Napping of gp100 epitopes recognized by TIL 1200 using gp100 deletion mutants.

Basically, two methods are commonly used in the art to map epitopes recognized by anti-tumor CTL.

1. According to the HLA binding motifs peptides can be synthesized that reside in the target protein. These peptides can then be loaded onto cells bearing the appropriate restriction element, and used as targets for CTL.
2. Generation of deletion mutants and expression of these deletion mutants in for example COS-7 cells together with the appropriate restriction element. These transfected cells are then co-cultured with CTL and target cell lysis or TNF-α/IFNγ production by the CTL are measured. Transfectants not recognized by the CTL do not express the peptide.

Both methods have been done in search for the epitopes of the invention.

TIL 1200 mediated lysis of peptide loaded T2 cells.

We have chemically synthesized gp100 peptides potentially recognized by TIL 1200. Peptides were synthesized by a solid phase strategy on an automated multiple peptide synthesizer (Abimed AMS 422) using Fmoc-chemistry (Nijman, 1993). Actual binding of the peptides to HLA-A2.1 was established with a recently described peptide binding assay making use of processing defective T2 cells (Nijman, 1993). This analysis resulted in the identification of gp100 derived peptides that strongly bind to HLA-A2.1. Subsequently, T2 cells loaded with the peptides that strongly bind to HLA-A2.1 were subjected to lysis by TIL 1200 using a standard chromium release assay. In this way the peptide L-L-D-G-T-A-T-L-R-L SEQ ID NO:4 has been identified according to this procedure..

EXAMPLE 4

Gp100 Epitope identified by deletion mapping

Gp100 cDNA was inserted into expression vectors pBJ1neo, pCMVneo (Baker et al, 1990) and pSVL. For the generation of a gp100 cDNA lacking the coding sequences for the peptide 457–466, PCR reactions were performed with the following combinations of oligonucleotides: 5'-CATGGAAGTGACTGTCTACC-3' SEQ ID NO:16 /5'-CTGAGCGAATTCGGAACCTGTAATACTTTCCG-3' SEQ ID NO:17, and 5'-CTGAGCGAATTCGTGAAG-AGACAAGTCCCCC-3' SEQ ID NO:18 /5'-TCACAGCATCATATGAGAGTAC-3' SEQ ID NO:19 using the full length gp100 cDNA as atemplate. PCR products were digested with Eco RI, ligated and served as a template for a nested PCR using the following primers: 5'-GCACAGGCCAACTGCAGA-3' SEQ ID NO:28 /5'-TTCAGTATCTGGTGCAGAAC-3' SEQ ID NO:29. The Kpn I-Cla I fragment from this PCR product was then exchanged with the corresponding fragment in pCMVgp100neo to generate pCMVgp100DEL454–481neo. Gp100 cDNA mutants DEL149–654 and DEL454–654 were obtained by deletion of the 1.7 kb Hind III and the 0.8 kb Eco RI fragments from pBJ1gp100DEL454–481neo, respectively. Gp100 cDNA mutants DEL100–654, DEL194–528 and DEL167–508 were obtained by deletion of the Bgl I-Sac I, Bamh HI-Bgl II and Apa I-Nsi I fragmnets from pSVLgp100 respectively.

BLM cells were transfected with 20 µg of pCMVgp100DEL454–481neo DNA according to the clacium phosphate coprecipitation procedure (Graham and van der Eb, 1973) using Calciumphosphate Transfection Systems (BRL, Gaithersburg, Md.) and were slected with 1 mg/ml G418 (Gibco, Paisley, Scotland UK).

COS-7 cells were contransfected with 5 µg of pBJ1HLA-A2.1neo and 5 µg of pBJ1 or pSVL plasmids containing either full length or deleted gp100 cDNAs using the DEAE-dextran/chloroquine method (Seed and Aruffo, 1987). After 48 hours of transfection COS-7 cells were used as stimulator cells in IFN-γ release experiments.

Release assays

Chromium release assays were performed as in Example 2.

For IFN-release assya $10^5$ TIL 1200 responder cells were incubated together with $5·10^4$ transiently transfected COS-7 stimulator cells in 300 µl medium in the presence of 100 U/ml IL-2 in a flat bottom 96 well microtiter plate. After 24 hours of incubation, 100 µl of supernatant was harvested and was screened for the presence of IFN-γ using a hIFN-γ-IRMA immunoradiometric assay kit (megenix Diagnostics SA, Fleurus, Belgium).

Results

FIG. 3A shows the gp100 cDNA deletion mutants that were generated. As shown in FIG. 3B, TIL 1200 specifically secreted IFN-γ when stimulated with COS-7 cells transfected with HLA-A2.1 and the full length gp100 cDNA. Again TIL 1200 reactivity was observed against the gp100DEL454–481 mutant. From the other gp100 deletion mutants, only the DEKL100–661 and DEL149–661 constructs were not recognized, thereby excluding the possibility that TIL 1200 was reactive with a peptide located N-terminal from amino acid position 148 in the gp100 protein. Also the C-terminal region of the gp100 protein protein could be excluded, because TIL 1200 reactivity could be observed using a mutant construct, DEL454–661, encoding the first 453 amino acids of gp100. From the observation that a construct coding within this N-terminal region upto amino acid 166 was able to stimulate TIL 1200 (DEL167–508), it was concluded that the epitope recognized was located between amino acids 148–166 of the gp100 protein.

HLA-A2.1 binding

Several motifs have been described for 9-mer or 10-mer peptides binding to HLA-A2.1 (Falk et al., 1991; Hunt et al., 1992; Ruppert et al., 1993) that were deduced from naturally processed and synthetic HLA-A2.1 binding peptides. The 148–166 region of the gp100 protein was screened against these motifs and a number of peptides were synthesized that fitted into a somewhat broader motif, including threonine residues at position two. These peptides were loaded onto HLA-A2.1+ T2 cells and tested for their ability to induce TIL 1200 mediated target cell lysis (FIG. 4A). The five tested peptides were all able to sensitize T2 cells for lysis by TIL 1200 when used at a concentration of 10 µg/ml. All these peptides contain the 8-mer peptide TWGQYWQV SEQ. ID. NO. 8, corresponding to gp100 amino acids 155–162. All peptides were titrated to evaluate their relative ability to sensitize T2 target cells for lysis by TIL 1200. FIG. 4B shows that the 9-mer peptide KTWGQYWQV SEQ. ID. NO. 22 can be recognized by TIL 1200 when applied at a concentration of 3 ng/ml, whereas the other peptides had to be applied at higher concentrations.

A comparison was made of the peptides KTWGQYWQV SEQ ID NO:30 (gp100 amino acids 155–162), LLDG-TATLRL SEQ ID NO:4 (gp100 amino acids 457–466) and YLEPGPVTA SEQ ID NO:31 (gp100 amino acids 280–288, identified by Cox et al., 1994) with three known viral epitopes presented in HLA-A2.1: the influenza matrix 58–66 peptide (Gotch et al., 1987), the HIV polymerase 510–518 peptide (Tsomides et al., 1991) and the HIV gp120 197–205 peptide (Dadaglio et al., 1991). The HLA-A2.1 binding capacity of the above mentioned epitopes was analyzed by means of an indirect binding assay using the processing defective cell line T2 (Nijman et al., 1993). Shortly: T2 cells were incubated with 12.5 µg of the epitopes. HLA-A2.1 stabilization at the cell surface was determined by flow cytometry using mAb BB7.2. The Fluorescence Index is expressed as the experimental mean fluorescence divided by the mean fluorescence that is obtained when T2 cells are incubated with a HLA-A2.1 non-binding peptide at a similar concentration.

Using this assay, a similar HLA-A2.1 stabilization with the gp100 280–288 epitope and the tested viral epitopes. Both epitopes of the invention (KTWGQYWQV SEQ ID NO:22 and LLDGTATLRL SEQ ID NO:4) bind with a somewhat lower affinity to HLA-A2.1 (FIG. 5). From this it is concluded that the gp100 epitopes bind to HLA-A2.1 with distinct affinities.

REFERENCES

Adema, G. J. and Baas, P. D. (1991) Biochem. Biophys. Res. Com 178, 985–992
Altschut, S. F., Gish, W., Miller, W., Myers, E. W. and Lipman, D. J. (1990) J. Mol. Biol. 215, 403–410
Anichini, A. et al. (1993), J. Exp. Med. 177, 989–998
Baker, S. J. (1990), Science 249, 912–915
Bean, M. A., Bloom, B. R., Herberman, R. B., Old, L. J., Oettgen, H. F., Klein, G. and Terry, W. D. (1975) Cancer Res. 35, 2902–2907
Brichard et al. (1993) J. Exp. Med. 178 489–495
Chirgwin, J. M., Przybyla, A. E., MacDonald, R. J. and Rutter, W. J. (1979) Biochemistry, 5294–5299
Cleveland, D. W., Fischer, S. G., Kirschner, M. W. and Laemmli, U. K. (1977) J. Biol. Chem. 253, 1102–1106
Cox, A. L, Skipper, J., Chen, Y., Henderson, R. A., Darrow, T. L., Shabanowitz, J., Engelhard, V. H., Hunt, D. F., Slingluff, C. A. (1994) Science 264, 716
Dadaglio, G., Leroux, A., Langlade-Demoyen, P., Bahraoui, E. M., Traincard, V., Fisher, R., Plata, F., (1991) J. Immunol. 147, 2302.
Devereux, J., Haeberli, P., and Smithies, O. (1984) Nucleic Acids Res. 12, 387
Eisinger, M. and Marco, O. (1982) Proc. Natl. Acad. Sci. USA 79, 2018–2022
Espevik and Nissen-Meyer (1986) J.Immunol.Methods 95, 99
Esclamado, R. M., Gown, A. M. and Vogel, A. M. (1986) Am. J. Surg. 152, 376–385
Falk, K. et al. (1991) Nature 351, 290
Felgner, P. L., Gadek, T. R., Holm, M., Roman, R., Chan, W., Wenz, M., Northrop, J. P., Ringold, G. M. and Danielsen, M. (1987) Proc. Natl. Acad. Sci. USA 84, 7413–7417
Fisher, B. et al. (1989), J. Clin. Oncol. 7, 250–261
Gotch, F., Rothbard, J., Howland, K., Townsend, A., McMichael A., (1987) Nature 326, 881
Graham, F. L. and van der Eb, A. J.(1973), Virology 52, 456
Green, M. R. (1991) Ann. Rev. Cell Biol. 7, 559–599
Haisma, H. J. et al, (1986) J. Nucl. med. 27, 1890
Hall, R. et al. (1984) Nature 311, 379–387
Hnatowich, D. J. et al. (1983) J. Immunol. Meth. 65, 147–157
Hunt, D. F. et al. (1992) Science 255, 1261
Jones, P. T. et al. (1986) Nature 321, 522–525
Katano, M., Saxton, R. E., Cochran, A. J. and Irie, R. F. (1984) J. Cancer Res. Clin. Oncol. 108, 197
Kim, R. Y. and Wistow, G. J. (1992) Exp. Eye Res. 55, 657–662
Köhler, G. and Milstein C., (1975) Nature 256; 495–497
Knuth, A. et al., (1992) Cancer Surveys 39–52
Kozak, M. (1987) Nucleic Acids Res. 15, 8125–8148
Ksander, B. R, Rubsamen, P. E., Olsen, K. R, Cousins, S. W. and Streilein, J. W. (1991) Investigative Ophtamology & Visual Science, 32, 3198–3208
Kwon, B. S., Halaban, R., Kim, G. S., Usack, L., Pomerantz, S. and Haq, A. K. (1987) Mol. Biol. Med. 4, 339–355
Kwon, B. S., Chintammaneni, C., Kozak, C. A., Copeland, N. G., Gilbert, D. J., Jenkins, N., Barton, D., Francke, U., Kobayashi, Y. and Kim K. K. (1991) Proc. Natl. Acad. Sci. USA, 88 9228–9232
Kyte, J. and Doolittle, R. F. (1982) J. Mol. Biol. 157, 105–132
Lenstra, J. A. et al. (1990), Arch Virol. 110, 1–24
Loenen, W. A. M., de Vries, E., Gravestein, L. A., Hintzen, R. Q., van Lier, R. A. W. and Borst, J. (1991) Eur. J. Immunol. 22, 447
MacPherson, (1973) Soft Agar Techniques, Tissue Culture Methods and Applications, Kruse and Paterson, eds., Academic Press, 276
Maniatis et al., (1982, 1989) Molecular Cloning: A Laboratory Manual, Cold Spring Harbor Laboratory
Mochii, M., Agata, K. and Eguchi, G. (1991) Pigment Cell Res. 4, 41–47
Old, L., Cancer Res. (1981) 41, 361–375
Nijman et al. (1993), Eur.J.Immunol. 23, 1215
Padgett, R.A., Grabowski, P. J., Konarska M. M., Seiler, S. and Sharp, P. A. (1986) Ann. Rev. Biochem. 55, 119–1150
Pearson, W. R. and Lipman, D. J. (1988) Proc. Natl. Acad. Sci. USA 85, 2444–2448
Proudfoot, N. J. and Brownlee, G. G. (1976) Nature 263, 211–214
Rodriquez, R. L. and Denhardt, D. T. (1988), ed., Vectors: A survey of molecular cloning vectors and their uses, Butterworths
Rosenberg, S. A. et al. (1986), Science 223, 1318–1321
Runppert, J. et al. (1993) Cell 74, 929
Ruskin, B. et al. (194) Cell 38, 317–331
Sanger, F., Nidden, S. and Coulson, A. R. (1977) Proc. Natl Acad. Sci. USA 74, 5463–5467
Schwartz, R. H. (1992) Cell 71, 1065–1068
Seed, B and Aruffo, A. A. (1987) Proc. Natl. Acad. Sci. USA 84, 3365
Shilyansky, J. et al., Proc. Natl. Acad. Sci. USA 91, 2829–2833, 1994.
Smit, N., Le Poole, I., van den Wijngaard, R., Tigges, A., Westerhof, W. and Das, P. (1993) Arch. Dermatol. Res. 285, 356–365
Topalian, S. L. et al. (1987), J. Immunol. Meth. 102, 127–141
Townsend, A. R. M. and Bodmer H., (1989), Ann. Rev. Immunol. 7, 601–624
Tsomides, T. J., Walker, B. D., Eisen, H. N. (1991) Proc. Natl. Acad. Sci. USA 88, 11276
van Muijen, G. N. P., Cornelissen, L. M. H. A., Jansen, C. F. J., Figdor, C. G., Johnson, J. P., Bröker, E. and Ruiter, D. J. (1991) Clin. Expl. Metast. 9, 259–272
Vennegoor, C., Hageman, Ph., van Nouhuijs, H., Ruiter, D. J., Calafat, J., Ringens, P. J. and Rumke, Ph. (1988) Am. J. Pathol. 130, 179–192
Vogel, A. M. and Esclamado, R. M. (1988) Cancer Res. 48, 1286–1294
von Heijne, G. (1986) Nucleic Acids Res. 14, 4683–4690

What is claimed is:

1. A peptide consisting of an amino acid sequence said amino acid sequence selected from the group consisting of SEQ ID NO:8, SEQ ID NO:20, and SEQ ID NO:23, in combination with a pharmaceutically acceptable carrier or diluent.

2. A peptide consisting of an amino acid sequence, said amino acid sequence selected from the group consisting of SEQ ID NO:8, SEQ ID NO:20, and SEQ ID NO:23.

3. The peptide of claim 2 wherein the amino acid sequence is that of SEQ ID NO:8.

4. The peptide of claim 2 wherein the amino acid sequence is that of SEQ ID NO:20.

5. The peptide of claim 2 wherein the amino acid sequence is that of SEQ ID NO:23.

6. An immunogenic carrier or marker coupled to the peptide of claim 2.

* * * * *

UNITED STATES PATENT AND TRADEMARK OFFICE
CERTIFICATE OF CORRECTION

PATENT NO.    : 6,500,919 B1
DATED         : December 31, 2002
INVENTOR(S)   : Gosse Jan Adema and Carl Gustav Figdor It is certified that error appears in the above-identified patent and that said Letters Patent is hereby corrected as shown below:

Column 1,
Line 4, centered on its own line, insert -- CROSS-REFERENCE TO RELATED APPLICATIONS -- and following this, starting its own paragraph, insert:
-- This application is a Continuing Patent Application of U.S. Serial No. 08/388,852, filed on February 19, 1995. -- and following this, centered on its own line insert
-- TECHNICAL FIELD --

Column 3,
Line 2, change "te" to -- to --

Column 4,
Line 41, change "acid" to -- acids --
Line 64, change "desoxyribonucleic" to -- deoxyribonucleic --

Column 6,
Line 66, change "POEM" to -- pGEM --

Column 10,
Lines 23-24, change "producti on" to -- produc-tion --

Column 11,
Line 62, change "underlied" to -- underlined --

Column 13,
Lines 31 and 32, underline "GAATTC"
Line 67, change "Winconsin" to -- Wisconsin --

Column 14,
Lines 32-33, change "p revious" to -- previous --

Column 15,
Line 61, change "acid" to -- acids --

Column 19,
Line 26, change "atemplate" to -- a template --
Line 39, change "fragmnets" to -- fragments --
Line 43, change "clacium" to -- calcium --
Line 56, change "assya" to -- assay --

UNITED STATES PATENT AND TRADEMARK OFFICE
CERTIFICATE OF CORRECTION

PATENT NO. : 6,500,919 B1
DATED : December 31, 2002
INVENTOR(S) : Gosse Jan Adema and Carl Gustav Figdor It is certified that error appears in the above-identified patent and that said Letters Patent is hereby corrected as shown below:

Column 20,
Line 13, delete "protein" (2nd occurrence)

Column 21,
Line 14, after "Biochemistry" and before the comma insert -- 18 --

Column 53,
Line 2, insert a comma after "sequence"

Signed and Sealed this

Ninth Day of September, 2003

JAMES E. ROGAN
*Director of the United States Patent and Trademark Office*